US006559287B1

(12) United States Patent
Bennett et al.

(10) Patent No.: US 6,559,287 B1
(45) Date of Patent: May 6, 2003

(54) ARTIFICIAL PROTEOGLYCANS

(75) Inventors: Kelly L. Bennett, Skillman, NJ (US); Edith A. Wolff, Plainsboro, NJ (US); Alejandro A. Aruffo, Belle Mead, NJ (US); Brad W. Greenfield, Edmonds, WA (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/235,230

(22) Filed: Jan. 21, 1999

Related U.S. Application Data
(60) Provisional application No. 60/072,416, filed on Jan. 24, 1998.

(51) Int. Cl.⁷ ........................ C07K 14/00; C07H 21/04; C12N 15/00
(52) U.S. Cl. .................. 530/395; 530/300; 530/350; 435/69.1; 435/69.7; 514/2; 424/9.34; 536/23.1
(58) Field of Search .................. 530/350, 300, 530/395; 435/69.1, 69.7; 514/2; 424/9.34; 536/23.1

(56) References Cited

U.S. PATENT DOCUMENTS

| | | | |
|---|---|---|---|
| 5,164,295 A | 11/1992 | Kisilevsky et al. et al. | 435/7.8 |
| 5,180,808 A | 1/1993 | Ruoslahti | 530/350 |
| 5,486,599 A | 1/1996 | Saunders et al. | 530/395 |
| 5,541,095 A | 7/1996 | Hirschberg et al. | 435/172.3 |
| 5,583,103 A | 12/1996 | Ruoslahti et al. | 514/8 |
| 5,585,467 A | 12/1996 | Lee et al. | 530/395 |
| 5,591,716 A | 1/1997 | Siebert et al. | 514/12 |
| 5,625,040 A | 4/1997 | Margolis et al. | 530/395 |

OTHER PUBLICATIONS

Fritz et al., *Two N–Acetylglucosaminyltransferases Catalyze the Biosynthesis of Heparin Sulfate*, J. Biol Chem. (1994), vol. 269, No. 46, pp. 28809–38814.
Zhang et al., *Accumulation of a Pentasaccharide Terminating in α–N–Acetylgucosamine in an Animal Cell Mutant Defective in Heparan Sulfate Biosynthesis*, J. Biol. Chem. (1995) vol. 270, No. 21, pp. 12557–12562.
Carter, *Site–Specific Proteolysis of Fusion Proteins*, ACS Symposium Ser. Protein Purification: Molec. Mech. Large–Scale Processes (1990), vol. 427, pp. 181–193.
Bennett et al. (1995) J. Cell Biol. 128, 687–698.
Jackson et al. (1995) J. Cell Biol. 128, 673–686.
Noble et al. (1993) J. Clin. Invest. 91, 2368–2377.
Henke et al. (1996) J. Clin. Invest. 97, 2541–2552.
Katoh et al. (1995) J. Exp. Med. 182, 419–429.
Miyake et al. (1990) J. Exp. Med. 172(1), 69–75.
Esko et al. (1996), Curr.Opin. Struct. Biol. 6:663–670.
Faham et al. (1996) Science 271, 1116–1120.
Arch et al. (1992) Science 257,682–685.
Screaton et al. (1992) Proc. Natl. acad. Sci. USA 89, 12160–12164.
Tanaka et al. (1993) Nature 361, 79–82.
Lindahl et al. (1994) Thrombosis Research 75, 1–32.
Weber et al. (1996) Science 271, 509–512.
Brown et al. (1991) J. Cell Biol. 113(1), 207–221.
Spiro et al. (1991) J. Cell Biol. 115, 1463–1473.
Galandrini et al. (1994) J. Immunol. 153, 21–31.
Denning et al. (1990) J. Immunol. 144, 7.
Kanner et al. (1992) J. Immunol. 148, 2023–2029.
Huet et al. (1989) J. Immunol. 143, 798–801.
Shimizu et al. (1989) J. Immunol. 143, 2457–2463.
Peach et al. (1993) J. Cell Biol. 122, 257–264.
Kinsella et al. (1986) J. Cell Biol. 102, 679–687.
Jalkanen et al. (1992) J. Cell Biol. 116(3), 817–825.
Bennett et al. (1995) J. Cell Biol. 131, 1623–1633.
Culty et al. (1990) J. Cell Biol. 111, 2765–2774.
Zhang et al. (1994) J. Biol Chem. 269, 19295–19299.
Uhlin–Hansen et al. (1993) J. Biol. Chem. 268, 17370–17376.
Fritz et al. (1994) J. Biol. Chem. 269, 300–307.
Jackson et al. (1992) J. Biol. Chem. 267, 4732–4739.
Chan et al. (1993) J. Biol. Chem. 268, 24655–24664.
Zhang et al. (1995) J. Biol. Chem. 270, 27127–27135.
Mann et al. (1990) J. Biol. Chem. 265(9), 5317–5323.
Aruffo et al. (1990) Cell 61(7), 1303–1313.
Gunthert et al. (1991) Cell 65, 13–24.
Ruoslahti et al. (1991) Cell 64, 867–869.
Springer et al. (1994) Cell 76, 301–314.
Goldstein et al. (1989) Cell 56, 1063–1072.
Gilat et al. (1996) Immunol. Today 17, 16–20.
Tanaka et al. (1993) Immunol Today 14, 111–115.
Haynes et al. (1989) Immunol. Today 10(12), 423–428.
Midura et al. (1994) Glycobiology 4, 333–342.
Salmivirta et al. (1996) FASEB J. 10, 1270–1279.
Ho et al. (1989) Gene 77, 51–59.
Maresh et al. (1994) Arch. Biochem. Biophys. 311, 95–102.
Jacobsson et al. (1986) Biochem. J. 240, 625–632.
Fransson et al. (1992) Biochem. Biophys. Acta 1137, 287–297.
Hardy (1989) Complex Carbohydrates, pp. 76–78, Academic Press, Bethesda, MD.
Lindahl (1989) Heparin and Heparin Sulphate Proteoglycans–an Overview, pp. 159–189, CRC Press, Boca Raton.
Greenfield et al. (1999) J. Bio Chem. 274:2511–2517.
Wolff et al. (1999) J. Bio. Chem. 274:2518–2524.

*Primary Examiner*—Yvonne Eyler
*Assistant Examiner*—Nirmal S. Basi
(74) *Attorney, Agent, or Firm*—Audrey F. Sher

(57) ABSTRACT

Novel articifial proteoglycans containing a GAG assembly site and a control sequence required for assembly, method for enhancing the biological activity of a glycosaminoglycan binding protein using artificial proteoglycans, DNA constructs of artificial proteoglycans. The artificial proteoglycans of the present invention are useful for preparations of adjuvants for vaccination, for targeting of chemokines to non-immunogenic tumor cells to enhance cellular anti-tumor response, for preparations designed to help promote wound healing, and for treatment of immunological disorders,including rheumatoid arthritis, asthma, chronic obstructive pulmonary disorder, Lupus, inflammatory bowel disease, psoriasis, osteoarthritis, and HIV infection.

1 Claim, 15 Drawing Sheets

V3_{E5/8aa}-Rg

V3 — Rg

SGSG SSSERSST

E5_{V3/8aa}-Rg

E5 — Rg

SG IDDDEDFI SG

E5V3_{wt}-Rg

E5 V3 — Rg

SGSG

E5V3_{mut}-Rg

E5 V3 — Rg

AGAG

V3_{wt}-V10-Rg

V3 V4 V5 V6 V7 V8 V9 V10 — Rg

SGSG

V3_{mut}-V10-Rg

V3 V4 V5 V6 V7 V8 V9 V10 — Rg

AGAG

SEQUENCE LISTING

<160> NUMBER OF SEQ ID NOS: 32

<210> SEQ ID NO 1
<211> LENGTH: 28
<212> TYPE: DNA
<213> ORGANISM: Homo sapiens

-continued

```
<400> SEQUENCE: 1
actagtacgt cttcaaatac catctcag                                        28

<210> SEQ ID NO 2
<211> LENGTH: 30
<212> TYPE: DNA
<213> ORGANISM: Homo sapiens

<400> SEQUENCE: 2
gggatccagg gtgctggaga taaaatcttc                                      30

<210> SEQ ID NO 3
<211> LENGTH: 27
<212> TYPE: DNA
<213> ORGANISM: Homo sapiens

<400> SEQUENCE: 3
actagtattg ttaaccgtga tggcacc                                         27

<210> SEQ ID NO 4
<211> LENGTH: 27
<212> TYPE: DNA
<213> ORGANISM: Homo sapiens

<400> SEQUENCE: 4
gggatccgtg gtagcaggga ttctgtc                                         27

<210> SEQ ID NO 5
<211> LENGTH: 24
<212> TYPE: DNA
<213> ORGANISM: Homo sapiens

<400> SEQUENCE: 5
actagtagga atgatgtcac aggt                                            24

<210> SEQ ID NO 6
<211> LENGTH: 39
<212> TYPE: DNA
<213> ORGANISM: Homo sapiens

<400> SEQUENCE: 6
gggatccgtg tcttggtctc ctgataagga acgattgac                            39

<210> SEQ ID NO 7
<211> LENGTH: 24
<212> TYPE: DNA
<213> ORGANISM: Homo sapiens

<400> SEQUENCE: 7
actagtgacc aagacacatt ccac                                            24

<210> SEQ ID NO 8
<211> LENGTH: 27
<212> TYPE: DNA
<213> ORGANISM: Homo sapiens

<400> SEQUENCE: 8
gggatcctct tgactcccat gtgagtg                                         27

<210> SEQ ID NO 9
<211> LENGTH: 24
<212> TYPE: DNA
<213> ORGANISM: Homo sapiens
```

```
<400> SEQUENCE: 9
actagtcact cacatgggag tcaa                                          24

<210> SEQ ID NO 10
<211> LENGTH: 27
<212> TYPE: DNA
<213> ORGANISM: Homo sapiens

<400> SEQUENCE: 10
gggatccgcc aaggccaaga gggatgc                                       27

<210> SEQ ID NO 11
<211> LENGTH: 66
<212> TYPE: DNA
<213> ORGANISM: Homo sapiens

<400> SEQUENCE: 11
gggatccagg gtgctggaga taaaatcttc atcatcatca atgcctgctc cagcaaaact   60
gaggtg                                                              66

<210> SEQ ID NO 12
<211> LENGTH: 28
<212> TYPE: PRT
<213> ORGANISM: Homo sapiens

<400> SEQUENCE: 12

Glu Asp Ile Tyr Pro Ser Asn Pro Thr Asp Asp Val Ser Ser Gly
  1               5                  10                  15

Ser Ser Ser Glu Arg Ser Ser Thr Ser Gly Gly Tyr
             20                  25

<210> SEQ ID NO 13
<211> LENGTH: 20
<212> TYPE: PRT
<213> ORGANISM: Homo sapiens

<400> SEQUENCE: 13

Asp Gln Asp Thr Phe His Pro Ser Gly Gly Ser His Thr Thr His Gly
  1               5                  10                  15

Ser Glu Ser Asp
             20

<210> SEQ ID NO 14
<211> LENGTH: 18
<212> TYPE: PRT
<213> ORGANISM: Homo sapiens

<400> SEQUENCE: 14

Glu Gly Gly Ala Asn Thr Thr Ser Gly Pro Ile Arg Thr Pro Gln Ile
  1               5                  10                  15

Pro Glu

<210> SEQ ID NO 15
<211> LENGTH: 28
<212> TYPE: PRT
<213> ORGANISM: Homo sapiens

<400> SEQUENCE: 15

Glu Pro Asn Glu Glu Asn Glu Asp Glu Arg Asp Arg His Leu Ser Phe
  1               5                  10                  15
```

Ser Gly Ser Gly Ile Asp Asp Asp Glu Asp Phe Ile
            20                  25

<210> SEQ ID NO 16
<211> LENGTH: 28
<212> TYPE: PRT
<213> ORGANISM: Homo sapiens

<400> SEQUENCE: 16

Glu Pro Asn Glu Glu Asn Glu Asp Glu Arg Asp Arg His Leu Ser Phe
 1               5                  10                  15

Ala Gly Ala Gly Ile Asp Asp Asp Glu Asp Phe Ile
            20                  25

<210> SEQ ID NO 17
<211> LENGTH: 15
<212> TYPE: PRT
<213> ORGANISM: Homo sapiens

<400> SEQUENCE: 17

Asn Val Asn Arg Ser Leu Ser Gly Asp Gln Asp Thr Phe His Pro
 1               5                  10                  15

<210> SEQ ID NO 18
<211> LENGTH: 54
<212> TYPE: DNA
<213> ORGANISM: Homo sapiens

<400> SEQUENCE: 18
agtgctgctc ctttcactgg aggagcctga tccagaaaag cttaggtgtc tgtc         54

<210> SEQ ID NO 19
<211> LENGTH: 51
<212> TYPE: DNA
<213> ORGANISM: Homo sapiens

<400> SEQUENCE: 19
tcctccagtg aaaggagcag cacttccagc accatttcaa ccacaccacg g            51

<210> SEQ ID NO 20
<211> LENGTH: 18
<212> TYPE: DNA
<213> ORGANISM: Homo sapiens

<400> SEQUENCE: 20
cggatttgaa tggcttgg                                                 18

<210> SEQ ID NO 21
<211> LENGTH: 30
<212> TYPE: DNA
<213> ORGANISM: Homo sapiens

<400> SEQUENCE: 21
gggatccagg gtgctggaag tgctgctcct                                    30

<210> SEQ ID NO 22
<211> LENGTH: 48
<212> TYPE: DNA
<213> ORGANISM: Homo sapiens

<400> SEQUENCE: 22
gataaaatct tcatcatcat cgatgccgct gctcacgtca tcatcagt                48

-continued

<210> SEQ ID NO 23
<211> LENGTH: 45
<212> TYPE: DNA
<213> ORGANISM: Homo sapiens

<400> SEQUENCE: 23
atcgatgatg aagattttat ctcaggaggt tacatctttt acacc            45

<210> SEQ ID NO 24
<211> LENGTH: 24
<212> TYPE: DNA
<213> ORGANISM: Homo sapiens

<400> SEQUENCE: 24
aagcttcgac gagccatggt tgct                                    24

<210> SEQ ID NO 25
<211> LENGTH: 54
<212> TYPE: DNA
<213> ORGANISM: Homo sapiens

<400> SEQUENCE: 25
gggatccccg ataaaatctt catcatcatc aataccgctg cttgggatac aggt   54

<210> SEQ ID NO 26
<211> LENGTH: 27
<212> TYPE: DNA
<213> ORGANISM: Homo sapiens

<400> SEQUENCE: 26
actagttctg tgtcttgaat gaccgct                                 27

<210> SEQ ID NO 27
<211> LENGTH: 33
<212> TYPE: DNA
<213> ORGANISM: Homo sapiens

<400> SEQUENCE: 27
gtacgggcca gatatacgcg ttgacattga tta                          33

<210> SEQ ID NO 28
<211> LENGTH: 27
<212> TYPE: DNA
<213> ORGANISM: Homo sapiens

<400> SEQUENCE: 28
actagttcgg atggtatagg cgccatc                                 27

<210> SEQ ID NO 29
<211> LENGTH: 8
<212> TYPE: PRT
<213> ORGANISM: Homo sapiens

<400> SEQUENCE: 29

Ile Asp Asp Asp Glu Asp Phe Ile
 1               5

<210> SEQ ID NO 30
<211> LENGTH: 4
<212> TYPE: PRT
<213> ORGANISM: Homo sapiens

<400> SEQUENCE: 30

```
Ser Gly Ser Gly
  1

<210> SEQ ID NO 31
<211> LENGTH: 6
<212> TYPE: PRT
<213> ORGANISM: Homo sapiens

<400> SEQUENCE: 31

Ser Gly Ser Gly Ser Gly
  1               5

<210> SEQ ID NO 32
<211> LENGTH: 8
<212> TYPE: PRT
<213> ORGANISM: Homo sapiens

<400> SEQUENCE: 32

Ser Ser Ser Glu Arg Ser Ser Thr
  1               5
```

ARTIFICIAL PROTEOGLYCANS

This application claims priority from provisional U.S. application Ser. No. 60/072,416, filed Jan. 24, 1998, which is incorporated herein by reference in its entirety.

BACKGROUND OF THE INVENTION

Heparan sulfate (HS) and chondroitin sulfate (CS) are glycosaminoglycans. Heparan sulfate and chondroitin sulfate modified proteoglycans have been shown to play an important role in regulating the function of a number of glycosaminoglycan (GAG) binding proteins which include growth factors and chemokines. For example, binding of basic fibroblast growth factor (b-FGF) to HS modified proteoglycans has been shown to increase local concentrations of the growth factor and prolong its half life. In addition, it appears that growth factor binding to the proteoglycan changes its conformation and facilitates its interaction with its receptor and also leads to receptor oligomerization enhancing signal transduction.

An example of a proteoglycan of current interest is CD44. CD44 is a widely distributed type I membrane protein which is capable of binding hyaluronan (HA), other extracellular matrix components and osteopontin. The interaction between CD44 and its ligands has been shown to participate in cell migration and activation. The exons encoding the CD44 gene can be variably spliced to give rise to multiple protein isoforms. Expression of these CD44 isoforms can be tissue specific, developmentally regulated and/or regulated by cell activation. Most of these isoforms arise from the variable splicing of exons encoding polypeptide fragments located in the extracellular region of CD44, downstream of the HA binding domain. Changes in the pattern of glycosylation of CD44 resulting from the addition of variably spliced exons, which are modified extensively with O-linked carbohydrates, can effectively modulate the HA binding activity of CD44. Likewise, different CD44 isoforms are modified with different GAG polymers including HS and CS.

SUMMARY OF THE INVENTION

The present invention concerns a method for enhancing the biological activity of a glycosaminoglycan binding protein comprising administering to a subject an effective amount of an artificial proteoglycan which is a recombinant fusion protein having a glycosaminoglycan assembly site comprising the sequence SG to which is bonded chondroitin sulfate or both chondroitin sulfate and heparan sulfate, wherein said recombinant fusion protein comprises:

(a) a first polypeptide which comprises a control sequence and the glycosaminoglycan assembly site wherein the control sequence and the assembly site result in modification of the polypeptide with chondroitin sulfate or both chondroitin sulfate and heparan sulfate, and (b) a second targeting polypeptide.

In another aspect, the present invention is directed to a method for modifying a protein having a glycosaminoglycan assembly site comprising the sequence SG, said method comprising recombinantly inserting nucleic acid encoding a proteoglycan or fragment thereof containing the control sequence into an expression vector encoding said protein such that said protein is expressed as a fusion protein comprising said proteoglycan or fragment thereof, and when said fusion protein is expressed in a host cell, said fusion protein is modified with chondroitin sulfate or both heparan sulfate and chondroitin sulfate.

Other aspects of the invention are artificial proteoglyans and chimeric nucleic acids encoding artificial proteoglycans.

BRIEF DESCRIPTION OF THE DRAWINGS

FIG. 5. CD44 immunoglobulin fusion proteins. Line drawings of the extracellular region of CD44. Boxes representing the variably spliced exons and standard exons are labeled V or E, respectively. The location of the SG sites is denoted by l symbol. The boxes representing the Ig domains in the fusion proteins are labeled Rg.

Amino acid sequence which were changed in the mutant proteins are shown underneath each construct in bold face.

Figure 6:
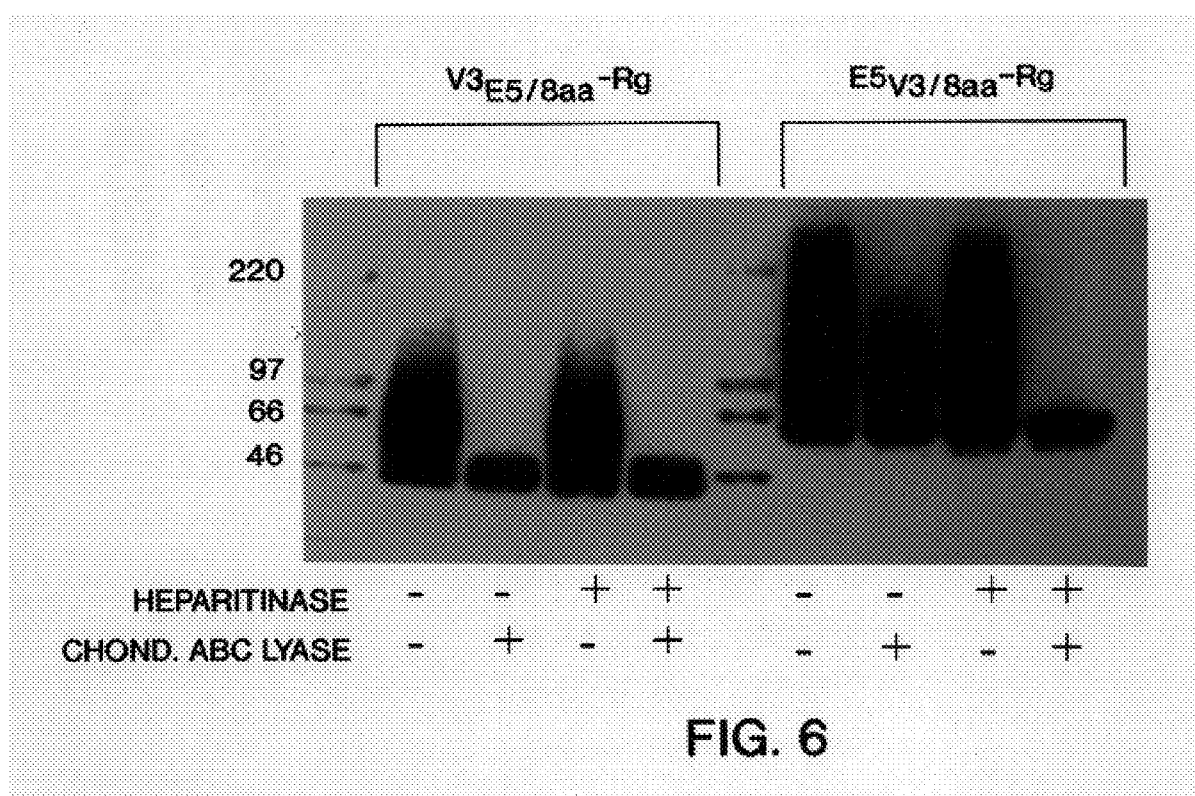

FIG. 6. The eight amino acids downstream of the SG site in CD44 exon V3 and E5 dictate the specificity of GAG modification. [$^{35}$S] NaHSO$_4$ labeled V3$_{E5/8aa}$-Rg and E5$_{V3/8aa}$-Rg proteins were recovered from the supernatant of COS cell transfectants, purified and divided equally into four aliquots. One aliquot was left untreated, the others were digested for one hour with either heparitinase, chondroitin ABC lyase, or with both enzymes. The proteins were then resolved by SDS-PAGE and analyzed by radiography.

Figure 7A:
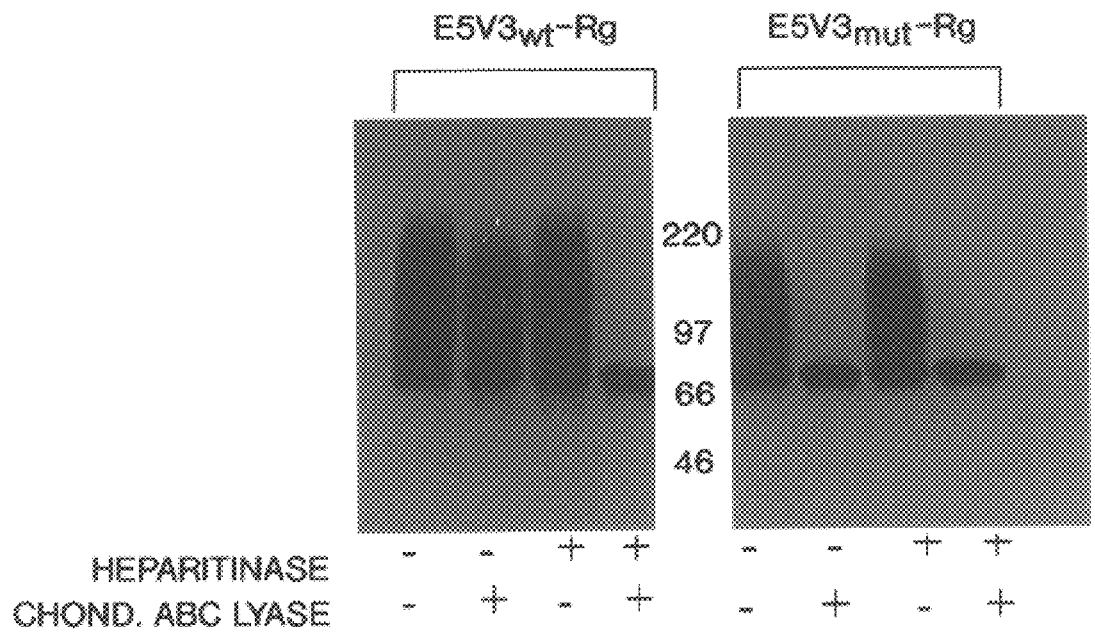
Figure 7B:
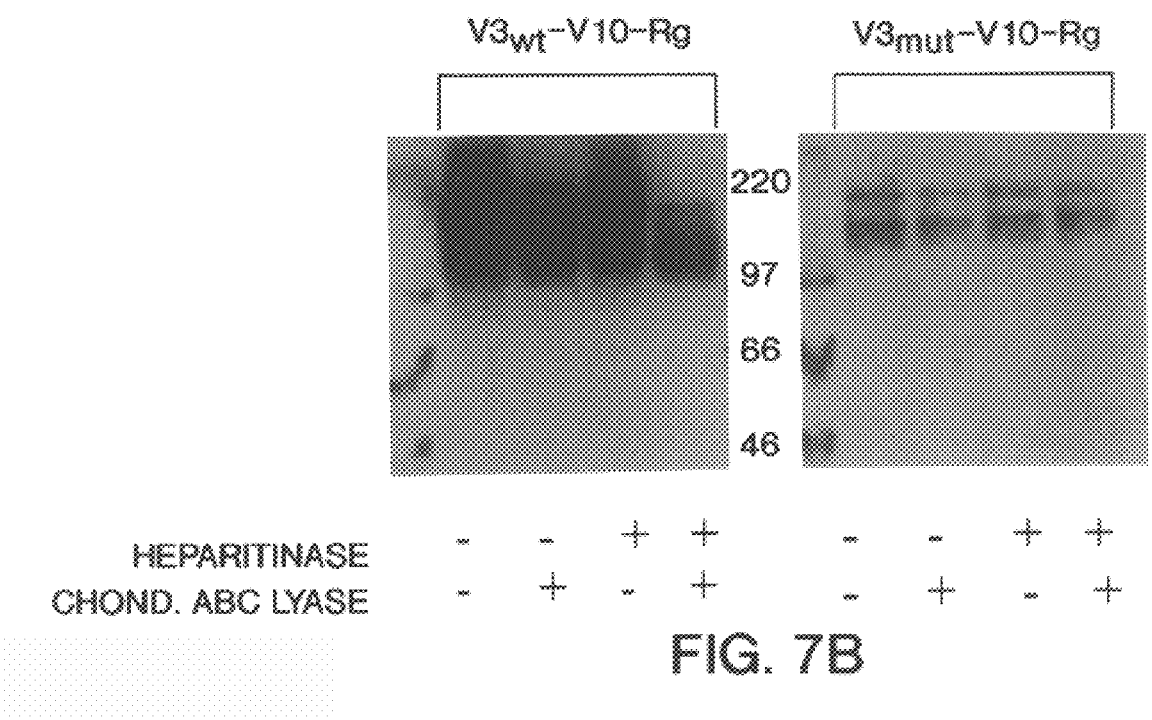

FIGS. 7A–7B. Residues in CD44 exon V3 do not direct the modification of distal sites with HS. [$^{35}$S] NaHSO$_4$ labeled E5V3$_{wt}$-Rg and E5V3$_{mt}$-Rg (FIG. 7A), and V3$_{wt}$-V10-Rg and V3$_{mt}$-V10-Rg (FIG. 7B) proteins were recovered from the supernatant of COS cell transfectants, purified and divided equally into four aliquots. One aliquot was left untreated, the others were digested for one hour with either heparitinase, chondroitin ABC lyase, or with both enzymes.

The proteins were then resolved by SDS-PAGE and analyzed by radiography.

Figure 8:
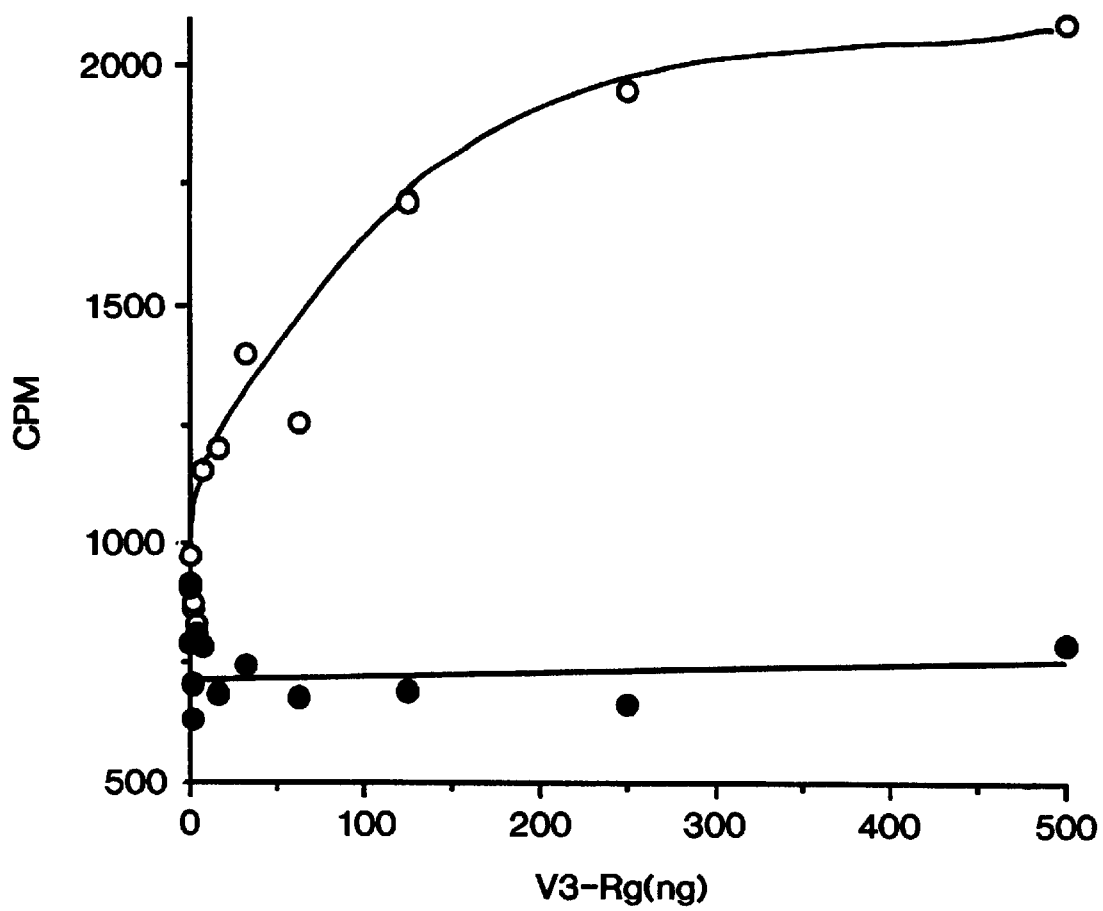

FIG. 8. Binding of $^{125}$I-bFGF to V3wt-Rg and V3mt-Rg. $^{125}$I-bFGF bound to increasing concentrations of V3wt-Rg (open circles) but not to V3mt-Rg (closed circles).

Figure 9:
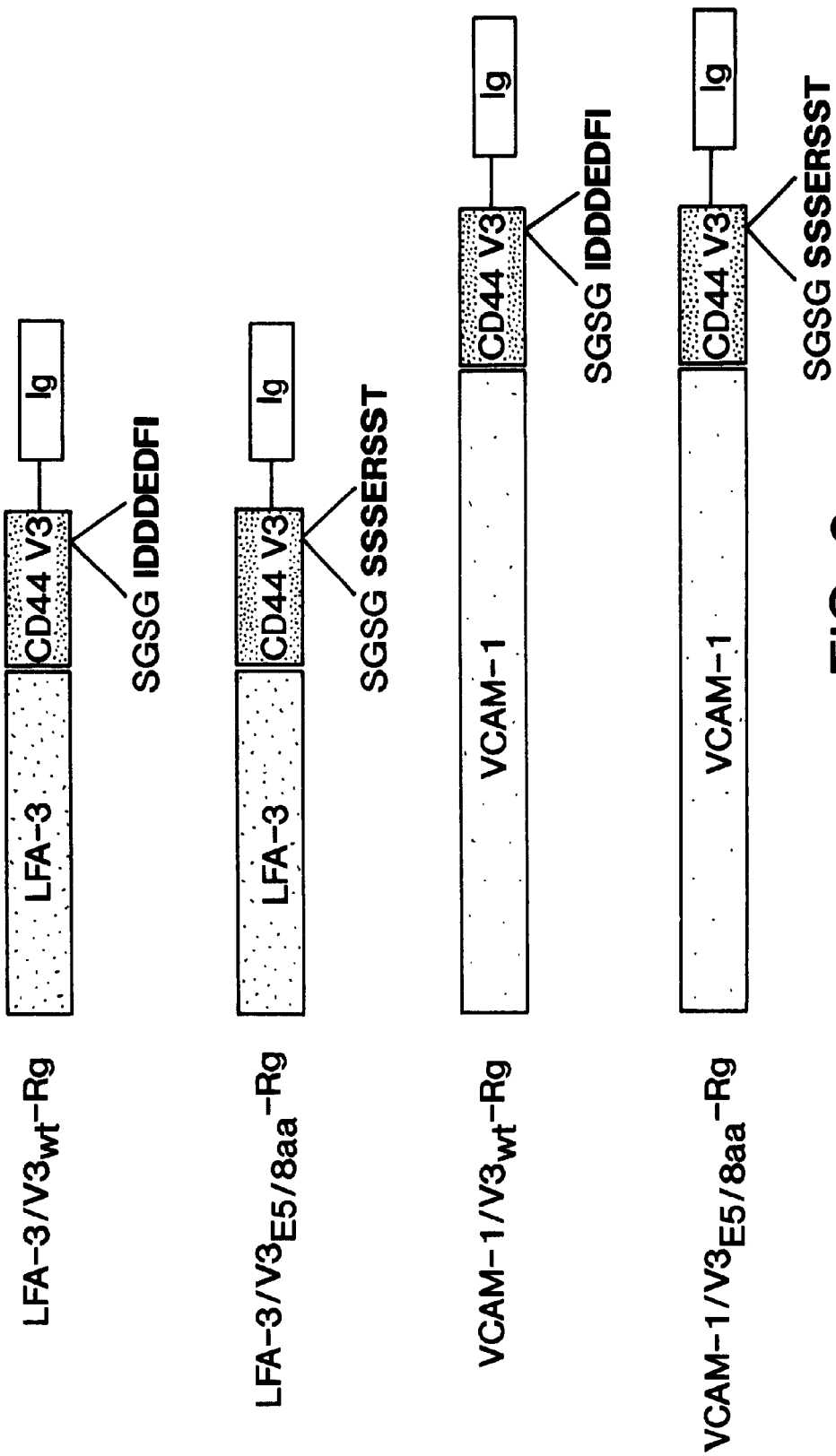

FIG. 9. Artificial proteoglycans. A) Line drawing of the LFA-3-Rg and VCAM-1-Rg fusion proteins containing wild type CD44 exon V3 ($V3_{wt}$) and CD44 exon V3 containing the eight amino acids found downstream of the first SG site in exon E5 ($V3_{E5/8aa}$). Boxes representing LFA-3, VCAM-1, CD44 and lg domains are labeled. The location of the single SG site in LFA-3 and the CD44 SG sites and downstream amino acid sequence are shown above and below the boxes representing each of the fusion proteins, respectively. B) Line drawing representation of recombinant CS and HS or CS modified proteoglycans.

Figure 10:
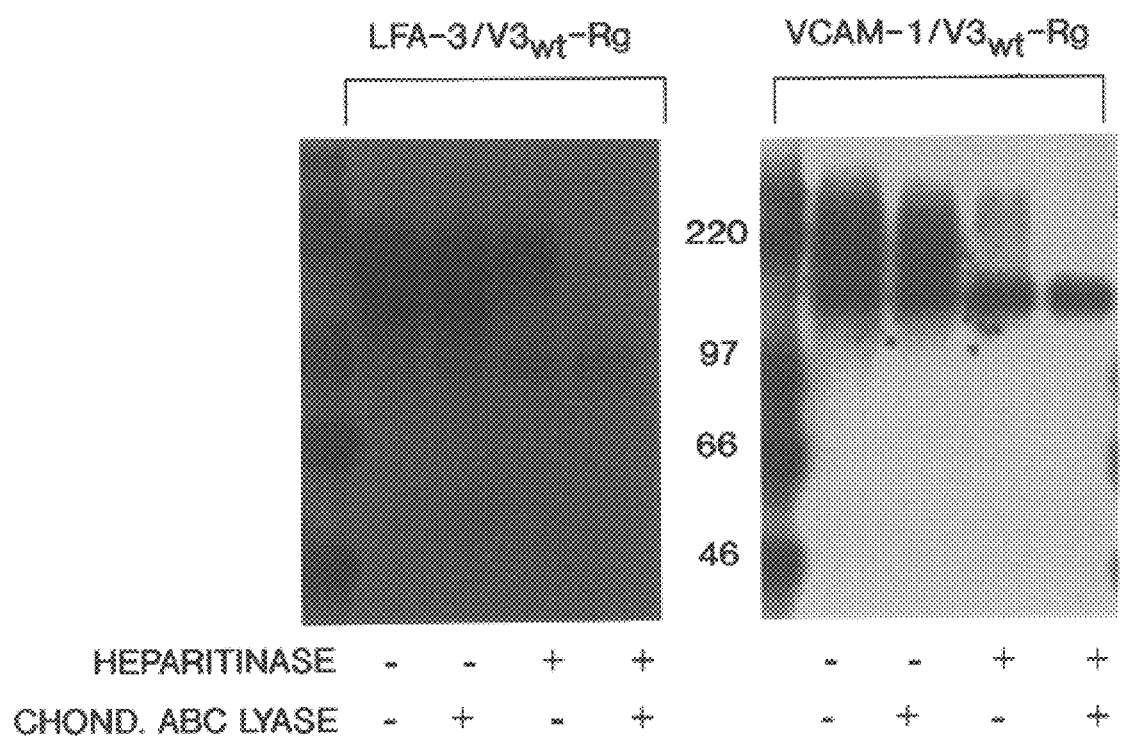

FIG. 10. A) Chimeric LFA-3, B) VCAM-1 proteins containing CD44 exon V3 are modified with CS and HS. [$^{35}$S] NaHSO$_4$ labeled LFA-3N3$_{wt}$-Rg protein was recovered from the supernatant of COS cell transfectants, purified and divided equally into four aliquots. One aliquot was left untreated, the others were digested for one hour with either heparitinase, chondroitin ABC lyase, or with both enzymes. The proteins were then resolved by SDS-PAGE and analyzed by radiography.

Figure 11:
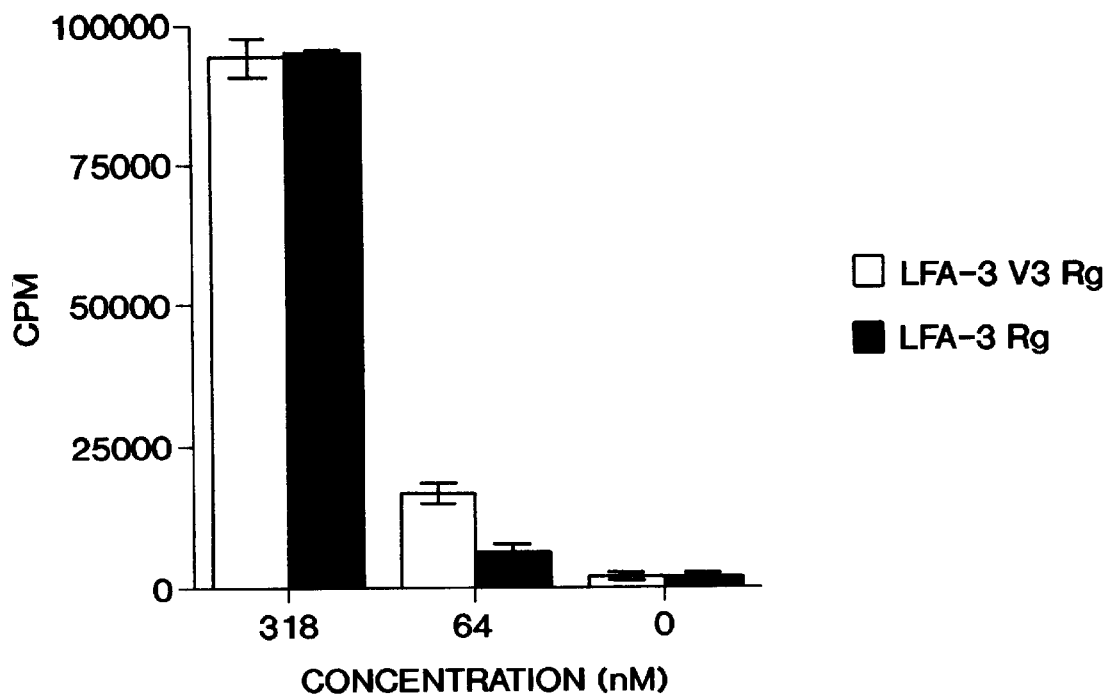

FIG. 11. Stimulation of T cells by GAG-modified and unmodified LFA-3. Both LFA-3-Rg (■) and LFA-3/V3$_{wt}$-Rg (□) induce proliferation of human T cells in the presence of suboptimal concentrations of anti-CD3 mAb. T cell proliferation was measured by $^3$H-thymidine uptake.

Figure 12A:
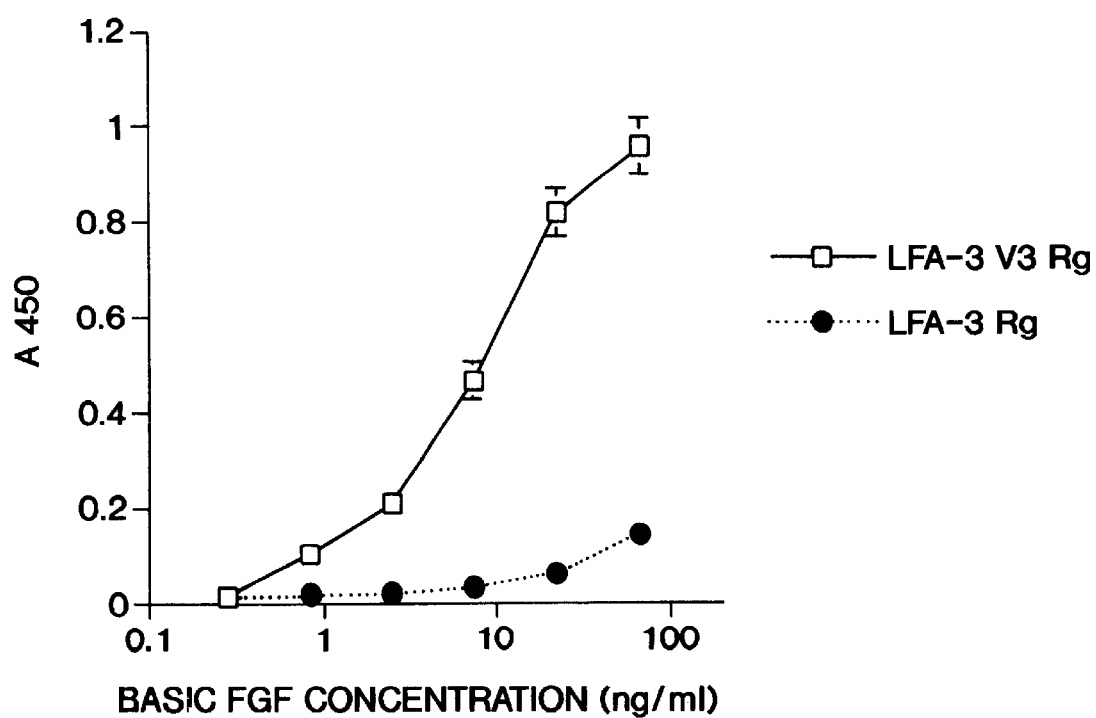
Figure 12B:
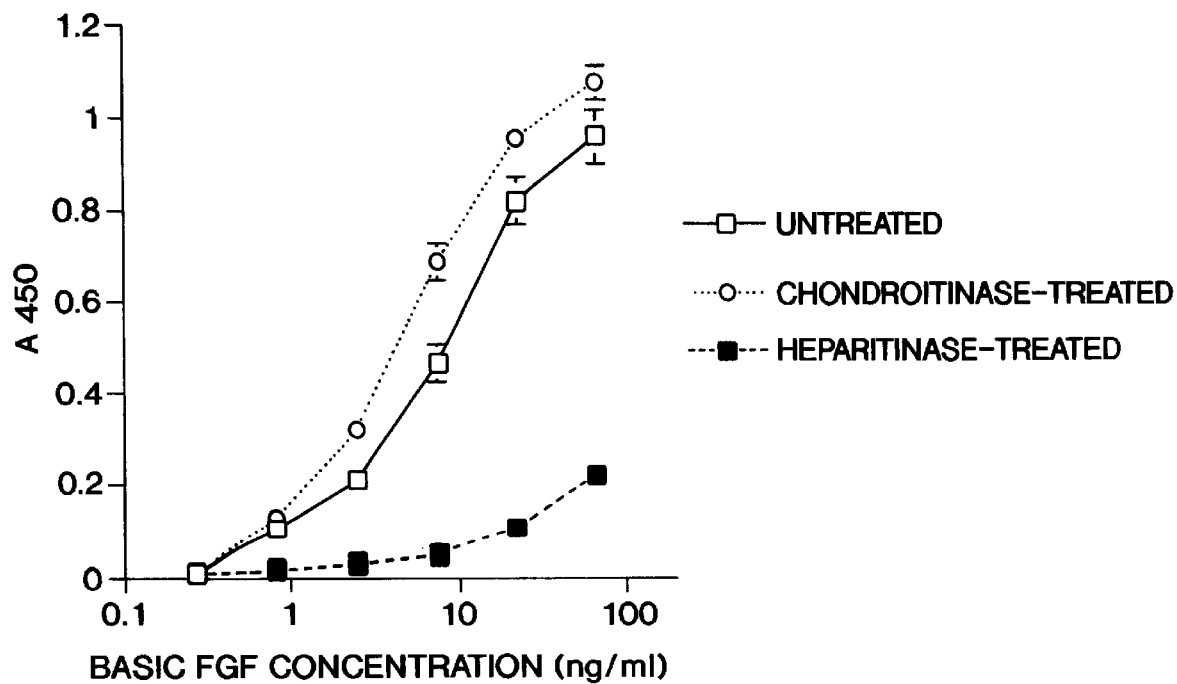
Figure 12C:
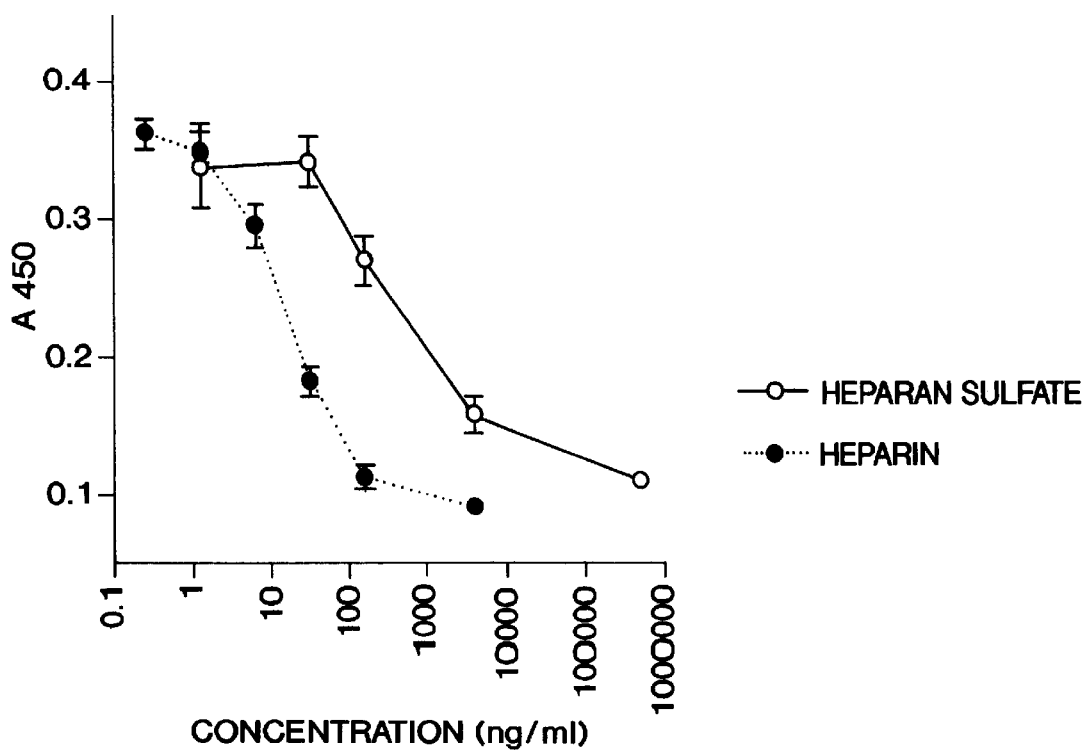

FIGS. 12A–12C. HS modified LFA-3 is capable of interacting with HS-binding growth factors. FIG. 12A shows ELISA binding activity of b-FGF to recombinant proteoglycan. B-FGF binds to GAG-modified LFA-3/V3$_{wt}$-Rg ( ) but not LFA-3-Rg (•). Binding was detected using goat antiserum specific for b-FGF, followed by donkey anti-goat lgG HRP. FIG. 12B shows analysis of b-FGF binding to enzyme-treated recombinant proteoglycan. B-FGF binding to LFA-3/V3$_{wt}$-Rg treated with heparitinase (|), chondroitinase (○), or untreated ( ) was compared by ELISA. FIG. 12C shows ELISA binding activity of b-FGF in the presence of heparin. Binding of b-FGF to LFA-3/V3$_{wt}$-Rg is blocked by heparin (•) and heparan sulfate (○).

Figure 13:
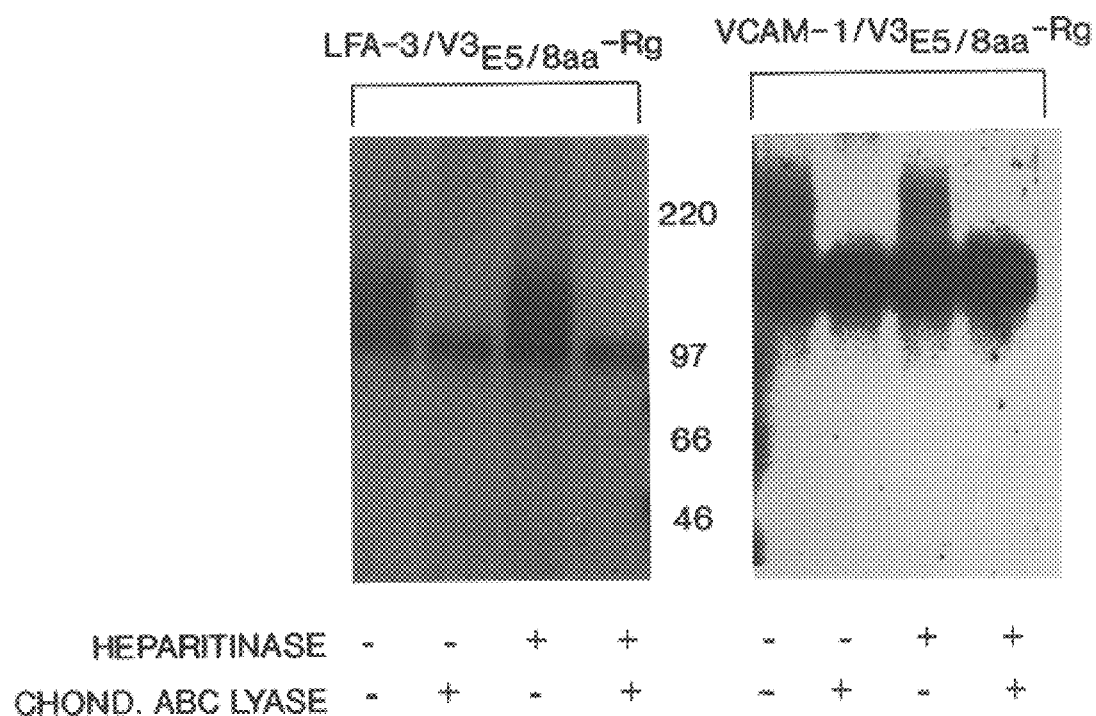

FIG. 13. Chimeric LFA-3 and VCAM-1 proteins containing the CD44 mutant V3 exon, V3$_{E5/8aa}$, are modified with CS. [$^{35}$S] NaHSO$_4$ labeled LFA-3/V3$_{E5/8aa}$ and VCAM-1/V3$_{E5/8aa}$-Rg protein were recovered from the supernatant of COS cell transfectants, purified and divided equally into four aliquots. One aliquot was left untreated, the others were digested for one hour with either heparitinase, chondroitin ABC lyase, or with both enzymes. The proteins were then resolved by SDS-PAGE and analyzed by radiography.

Figure 14A:
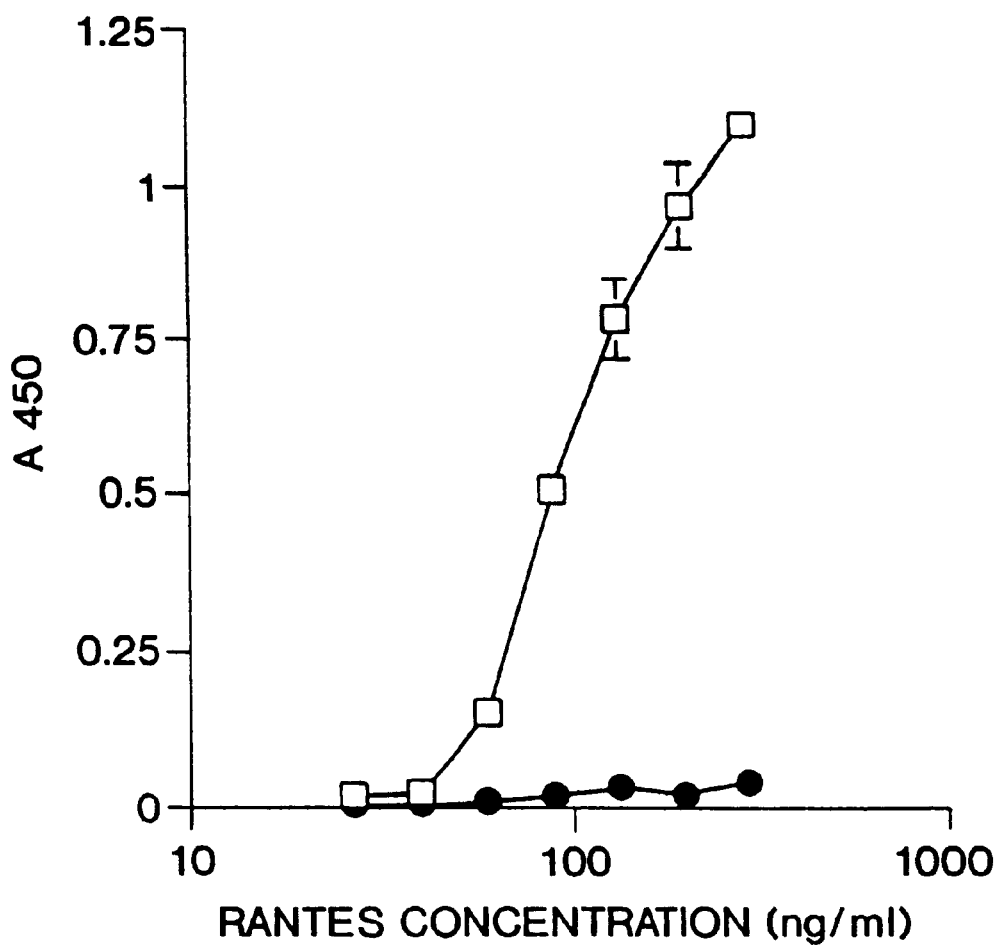
Figure 14B:
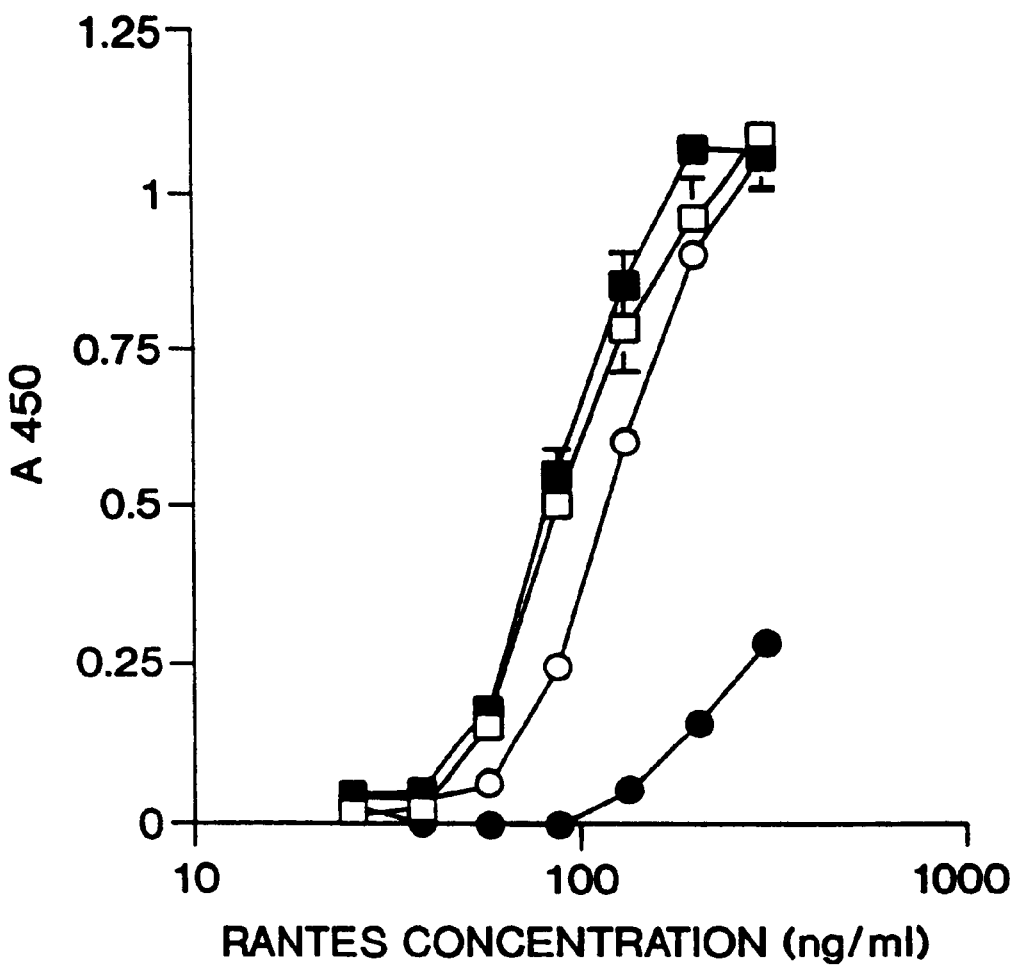

FIGS. 14A–14B. FIG. 14A shows GAG-modified LFA-3 interacts with chemokines. The binding activity of the chemokine RANTES to recombinant artificial proteoglycan was measured by ELISA. RANTES binds to GAG-modified LFA-3/V3$_{wt}$-Rg ( ) but not LFA-3-Rg ( ). FIG. 14B shows analysis of RANTES binding to enzyme-treated artificial proteoglycan. The binding activity of RANTES to LFA-3/V3$_{wt}$-Rg treated with heparitinase ( ), chondroitin ABC lyase ( ), both enzymes ( ), or untreated ( ) was tested by ELISA.

DETAILED DESCRIPTION OF THE INVENTION

The important role which proteoglycans play in regulating the function of HS-binding growth factors and chemokines has long been established. The artificial proteoglycans of the present invention can be used to target proteoglycans to a given site and thereby cause the local accumulation of GAG-binding proteins. Thus, the artifical proteoglycans of the invention are useful in preparations of adjuvants for vaccination, in the targeting of chemokines to non-immunogenic tumor cells to enhance cellular anti-tumor response, in preparations designed to help promote wound healing and for treatment of immunological disorders including rheumatoid arthritis, asthma, chronic obstructive pulmonary disorder, Lupus, inflammatory bowel disease, psoriasis, osteoarthritis, and HIV infection. In addition, the artifical proteoglycans of the invention can enhance the half life of non-GAG binding growth factors. Therefore, in the method of the invention for enhancing the biological activity of GAG binding proteins, said biological activity can be anti-tumor activity, vaccine adjuvant activity, wound healing, growth, and the like.

It is known that proteoglycans that are modified with GAGs contain the minimal assembly site sequence SG within an appropriate tertiary structure. The SG assembly site is the point at which the GAG is added to the proteoglycan. Proteoglycans that are modified with GAGs have a control sequence. We define control sequence as the sequence that defines the tertiary structure and allows for GAG assembly. In the case of HS, the control sequence includes a specific sequence that directs HS assembly. In the case of CS, the control sequence is believed to be just that which defines the tertiary structure (LindahI, U., Lidholt, K., Spillman, D., and Kjellan, L. (1994) Thrombosis Research 75, 1–32). From the data available in Zhang et. al., (1995) J. Biol. Chem. 270, 27127–27135, we have deduced that when a proteoglycan is modified with CS there is an area of 24 amino acids surrounding the assembly site in which is found the control sequence. The 24 amino acids includes the amino acids of the assembly site. We have also deduced that when a proteoglycan is modified with both CS and HS, there is an area of 24 amino acids surrounding the assembly site in which is found the control sequence, and the control sequence comprises at least three acidic amino acids and at least one hydrophobic amino acid.

It is known that CD44 isoforms containing variably spliced exon V3 are modified with HS and with CS at an assembly site. CD44 V3 contains the SG assembly site and a control sequence. The CD44 V3 control sequence defines an appropriate tertiary structure and includes a specific sequence, IDDEDFI, which we have identified. CD44 isoforms containing exon E5 are modified with CS. CD44 E5 contains the SG assembly site and a control sequence that defines an appropriate tertiary structure.

Examples of GAG binding proteins whose activity is enhanced by artificial proteoglycans of the invention include growth factors, chemokines, cytokines, enzymes, adhesion molecules, and the like. Examples of growth factors include b-FGF, a-FGF, AR, HB-EGF, TGFβ and the like. Examples of chemokines include RANTES, PF4, MIP-1β, and the like. Examples of cytokines include IL-8, GM-CSF, and the like. Examples of enzymes include Lipoprotein lipase, elastase, superoxide dismutase, and the like. Examples of adhesion molecules include laminin, thrombospondin, tenascin, and the like.

The GAG binding proteins which activity is enhanced by the artificial proteoglycans of the invention can be endogenous in the treated subject, or can be administered separately. If administered separately, the GAG binding protein can be administered before, after, or concurrent with the artificial proteoglycan.

The artificial proteoglycans of the invention have at least one glycosoaminoglycan assembly site. The glycosoaminoglycan assembly site comprises the sequence SG. The glycosoaminoglycan assembly site optionally contains multiple SG sequences such as SGSG (SEQ.ID.NO.:30), SGSGSG (SEQ.ID.NO.:31), and the like.

The glycosoaminoglycan assembly site is part of the first polypeptide making up the artificial proteoglycan. The first polypeptide can be adjacent to the second polypeptide, or the first polypeptide can be contained within the second polypeptide.

The first polypeptide making up the artificial proteoglycan of the present invention comprises a control sequence and a glycosaminoglycan assembly site wherein the control sequence and the glycosaminoglycan assembly site result in modification of the polypeptide with chondroitin sulfate or both chondroitin sulfate and heparan sulfate. In one embodiment of the inventions, the control sequence is contained within 24 amino acids surrounding the glycosaminoglycan assembly site. In another embodiment of the invention, the control sequence is contained within 24 amino acids surrounding the glycosaminoglycan assembly site and comprises at least three acidic amino acids and at least one hydrophobic amino acid. In the embodiments described in which the control sequence is contained within 24 amino acids surrounding the glycosaminoglycan assembly site, the control sequence is preferably contained within 11 amino acids on either side of the glycosaminoglycan assembly site. In the embodiment described in which the control sequence comprises at least three acidic amino acids and at least one hydrophobic amino acid, the possible acidic amino acids include aspartic acid and glutamic acid, and the possible hydrophobic amino acids include phenylalanine, tyrosine, leucine, isoleucine and tryptophan. In a preferred embodiment, the control sequence comprises IDDDEDFI (SEQ.ID.NO.:29).

The first polypeptide can be a wide variety of polypeptides provided that the required control sequence is present. Thus, the first polypeptide can also contain a wide variety or other sequences depending on the source of the polypeptide and the intended biological function. It is preferred that the first polypeptide is a proteoglycan of fragment thereof. Examples of such polypeptides include receptors, antibodies, antibody fragments, receptor binding ligands, and the like. Specific examples include perlecan, fibroglycan, syndecan-3, betaglycan, syndecan-1, and the like. Preferred first polypeptides include CD44 exon V3 or CD44 exon E5, or fragments thereof containing the required control sequences.

The second targeting polypeptide making up the fusion protein artificial proteoglycan can be any polypeptide or fragment thereof which is capable of binding to the desired target, referred to herein as a "targeting polypeptide". Classes of such second binding proteins include antibodies, receptors, receptor binding ligands, and the like. Specific examples of second targeting proteins include LFA-3, VCAM-1, B7, αCD3, and the like.

Specific examples of artificial proteoglycans of the invention include the constructs LFA-3/V3$_{wt}$-Rg, LFA-3/V3$_{E5/8aa}$-Rg, VCAM-1/V3$_{wt}$-Rg, VCAM-1/V3$_{E5/8aa}$-Rg, and LFA-3/E5$_{wt}$-Rg as described in the Examples section hereof.

In the therapeutic methods of the invention, the form of administration of the artificial proteoglycan and GAG binding protein (if administered) can be any form known in the pharmaceutical art. The amount of artificial proteoglycan and GAG binding protein to be administered would depend in part on the age, weight, and general condition of the patient. Typically, a patient would be closely monitored by a physician who would determine if the dosage amount or regimen of artificial proteoglycan and GAG binding protein being administered was effective and well tolerated. Artifical proteoglycans and GAG binding proteins would be administered either alone or admixed with a pharmaceutically acceptable carrier. Administration can be parenteral or enteral depending upon the dosage form and the needs of the patient.

The effective amount of the artifical proteoglycan depends upon many factors such as the intended biological effect as well as the age, weight, sex, health, etc. of the subject. For wound healing, a typical effective amount is about 1 μg to about 50 mg per kg of body weight per day. For anti-tumor activity, a typical effective amount is about 1 μg to about 50 mg per kg of body weight per day. When used as a vaccine adjuvant, the artificial proteoglycan typically comprises about 0.00001 to about 1 weight percent of the total vaccine composition. For treatment of immunological disorders, a typical effective amount is about 1 μg to about 50 mg per kg of body weight per day. Therefore, the present invention is also directed to a method for enhancing wound healing comprising administering to a subject about 1 μg to about 50 mg per kg of body weight per day of the artificial proteoglycan of the invention. Also, the present invention is directed to a method for enhancing the cellular anti-tumor response comprising administering to a subject about 1 μg to about 50 mg per kg of body weight per day the artificial proteoglycan of the invention. Also, the present invention is directed to a vaccine composition comprising about 0.00001 to about 1 weight percent of the artificial proteoglycan of the invention, based on total composition weight. Also, the present invention is directed to a method for treating immunological disorders including rheumatoid arthritis, asthma, chronic obstructive pulmonary disorder, Lupus, inflammatory bowel disease, psoriasis, osteoarthritis, and HIV infection comprising administering to a subject about 1 μg to about 50 mg per kg of body weight per day the artificial proteoglycan of the invention.

If GAG binding protein is to be administered, the same factors considered above for administering the artificial proteoglycan should be taken into account. In general, the dosages and amounts of GAG binding protein are the same or similar to the dosages and amounts of artificial proteoglycans recited above.

The artificial proteoglycan of the invention can be prepared using standard recombinant nucleic acid technology known in the art to prepare nucleic acid encoding the proteoglycan and expressing the proteoglycan in a suitable host cell. Preferably, the nucleic acid molecule is a DNA molecule and the nucleic acid sequence is a DNA sequence. All DNA sequences are represented herein by formulas whose left to right orientation is in the conventional direction of 5' to 3'.

It is also contemplated that the present invention encompasses modified sequences. As used in the present application, the term "modified", when referring to a nucleotide or polypeptide sequence, means a nucleotide or polypeptide sequence which differs from the wild-type sequence found in nature.

The DNA sequences of the present invention can be obtained using various methods well-known to those of ordinary skill in the art. At least three alternative principal methods may be employed:

(i) the isolation of a double-stranded DNA sequence from genomic DNA or complementary DNA (cDNA) which contains the sequence;

(2) the chemical synthesis of the DNA sequence; and
(3) the synthesis of the DNA sequence by polymerase chain reaction (PCR).

In the first approach, a genomic or cDNA library can be screened in order to identify a DNA sequence coding for all or part of the desired peptide. Various techniques can be used to screen the genomic DNA or cDNA libraries.

For example, labeled single stranded DNA probe sequences duplicating a sequence present in the target genomic DNA or cDNA coding for all or part of the desired peptide can be employed in DNA/DNA hybridization procedures carried out on cloned copies of the genomic DNA or cDNA which have been denatured to single stranded form.

A genomic DNA or cDNA library can also be screened for a genomic DNA or cDNA coding for all or part of the desired peptide using immunoblotting techniques.

In one typical screening method suitable for either immunoblotting or hybridization techniques, the genomic DNA library, which is usually contained in a vector, or cDNA library is first spread out on agar plates, and then the clones are transferred to filter membranes, for example, nitrocellulose membranes. A DNA probe can then be hybridized or an antibody can then be bound to the clones to identify those clones containing the genomic DNA or cDNA coding for all or part of the desired peptide.

In the second approach, the DNA sequences of the present invention coding for all or part of the desired peptide can be chemically synthesized. For example, the DNA sequence coding for the artificial proteoglycan can be synthesized as a series of 100 base oligonucleotides that can be sequentially ligated (via appropriate terminal restriction sites or complementary terminal sequences) so as to form the correct linear sequence of nucleotides.

In the third approach, the DNA sequences of the present invention coding for all or part of the desired peptide can be synthesized using PCR. Briefly, pairs of synthetic DNA oligonucleotides at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, White et al., Trends Genet. 5, 185–189 (1989).

The DNA sequences of the present invention coding for all or part of the desired peptides can also be modified (i.e., mutated) to prepare various mutations. Such mutations may be either degenerate, i.e., the mutation changes the amino acid sequence encoded by the mutated codon, or non-degenerate, i.e., the mutation does not change the amino acid sequence encoded by the mutated codon. These modified DNA sequences may be prepared, for example, by mutating the desired DNA sequence so that the mutation results in the deletion, substitution, insertion, inversion or addition of one or more amino acids in the encoded polypeptide using various methods known in the art. For example, the methods of site-directed mutagenesis described in Morinaga et al., Bio/Technol. 2, 636–639 (1984), Taylor et al., Nucl. Acids Res. 13, 8749–8764 (1985) and Kunkel, Proc. Natl. Acad. Sci. USA 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). In addition, disruption, deletion and truncation methods as described in Sayers et al., Nucl. Acids Res. 16, 791–802 (1988) may also be employed.

Both degenerate and non-degenerate mutations may be advantageous in producing or using the polypeptides of the present invention. For example, these mutations may permit higher levels of production, easier purification, or provide additional restriction endonuclease recognition sites. All such modified DNA and polypeptide molecules are included within the scope of the present invention.

The present invention further concerns expression vectors comprising a DNA sequence coding for the artificial proteoglycan. The expression vectors preferably contain all or part of one of the DNA sequences having the nucleotide sequences encoding CD44 exon V3 or CD44 exon E5. Further preferred are expression vectors comprising one or more regulatory DNA sequences operatively linked to the DNA sequence coding for the proteoglycan. As used in this context, the term "operatively linked" means that the regulatory DNA sequences are capable of directing the replication and/or the expression of the DNA sequence coding for the proteoglycan.

Expression vectors of utility in the present invention are often in the form of "plasmids", which refer to circular double stranded DNA loops which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front (i.e., upstream of) the DNA sequence encoding the proteoglycan and followed by the DNA sequence encoding the proteoglycan. The DNA sequence coding for the proteoglycan is followed by transcription termination sequences and the remaining vector. The expression vectors may also include other DNA sequences known in the art; for example, stability leader sequences which provide for stability of the expression product, secretory leader sequences which provide for secretion of the expression product, sequences which allow expression of the proteoglycan to modulated (e.g., by the presence or absence of nutrients or other inducers in the growth medium), marking sequences which are capable of providing phenotypic selection in transformed host cells, stability elements such as centromeres which provide mitotic stability to the plasmid, and sequences which provide sites for cleavage by restriction endonucleases. The characteristics of the actual expression vector used must be compatible with the host cell which is to be employed. Suitable promoters include, for example, the SV-40 promoter. It is also preferred that the expression vector include a sequence coding for a selectable marker. The selectable marker is preferably $Amp^R$ or $Tet^R$. All of these materials are known in the art and are commercially available.

Particularly preferred are the expression vectors designated CDM8 and pD18, described herein below and in FIG. 10, which contains the DNA sequence coding for LFA-3/V3wt-Rg.

Suitable expression vectors containing the desired coding and control sequences may be constructed using standard recombinant DNA techniques known in the art, many of which are described in Sambrook et al. Molecular Cloning: A Laboratory Manual, 2nd edition, Cold Spring Harbor Laboratory, Cold Spring Harbor, N.Y. (1989).

The present invention additionally concerns host cells containing an expression vector which comprises a DNA sequence coding for the artificial proteoglycan of the invention. The host cells preferably contain an expression vector which comprises all or part of one of the DNA sequence having the nucleotide sequences substantially as shown in FIG. 5. Further preferred are host cells containing an expression vector comprising one or more regulatory DNA sequences capable of directing the replication and/or the expression of and operatively linked to a DNA sequence coding for the proteoglycan. Suitable host cells include COS cells and CHO cells (DG44).

Expression vectors may be introduced into host cells by various methods known in the art. For example, transfection of host cells with expression vectors can be carried out by the polyethylene glycol mediated protoplast transformation method. However, other methods for introducing expression vectors into host cells, for example, electroporation, biolistic injection, or protoplast fusion, can also be employed.

Once an expression vector has been introduced into an appropriate host cell, the host cell may be cultured under conditions permitting expression of the desired polypeptide.

Host cells containing an expression vector which contains a DNA sequence coding for the proteoglycan may be identified by one or more of the following six general approaches: (a) DNA-DNA hybridization; (b) the presence or absence of marker gene functions; (d) assessing the level of transcription as measured by the production of proteoglycan mRNA transcripts in the host cell; (d) detection of the gene product immunologically; (e) colorimetric detection; and (f) enzyme assay, (d) being the preferred method of identification.

In the first approach, the presence of a DNA sequence coding for the proteoglycan can be detected by DNA-DNA or RNA-DNA hybridization using probes complementary to the DNA sequence.

In the second approach, the recombinant expression vector host system can be identified and selected based upon the presence or absence of certain marker gene functions (e.g., dihydorfolate reductase (mehotrexate is the selection component), etc.). A marker gene can be placed in the same plasmid as the DNA sequence coding for the proteoglycan under the regulation of the same or a different promoter used to regulate the proteoglycan coding sequence. Expression of the marker gene in response to induction or selection indicates the presence of the entire recombinant expression vector which carries the DNA sequence coding for the proteoglycan.

In the third approach, the production of proteoglycan mRNA transcripts can be assessed by hybridization assays. For example, polyadenylated RNA can be isolated and analyzed by Northern blotting or nuclease protection assay using a probe complementary to the RNA sequence. Alternatively, the total nucleic acids of the host cell may be extracted and assayed for hybridization to such probes.

In the fourth approach, the expression of the proteoglycan can be assessed immunologically, for example, by Western blotting.

In the fifth approach, the expression of the proteoglycan can be assessed by complementation analysis.

In the sixth approach, expression of the proteoglycan can be measured by assaying for proteoglycan activity using known methods.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977) may be employed.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns a method for producing the artificial proteoglycan comprising culturing a host cell containing an expression vector capable of expressing the proteoglycan. Preferably the expression vector is pD18.

The present invention is also directed to the artificial proteoglycan. All amino acid residues identified herein are in the natural L-configuration. In keeping with standard polypeptide nomenclature, *J. Biol. Chem.* 243, 3557–3559 (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

All amino acid sequences are represented herein by formulas whose left to right orientation is in the conventional direction of amino-terminus to carboxy-terminus.

It is preferred that the artificial proteoglycan of the invention be obtained by production in eukaryotic host cells expressing a DNA sequence coding for the proteoglycan. For example, the DNA sequence of CD44 exon V3 may be synthesized using PCR as described above and inserted into a suitable expression vector, which in turn may be used to transform a suitable host cell. The recombinant host cell may then be cultured to produce the proteoglycan modified with, in the case of CD44 V3, HS and CS. Techniques for the production of polypeptides by these means are known in the art, and are described herein.

The polypeptides produced in this manner may then be isolated and purified to some degree using various protein purification techniques. For example, chromatographic procedures such as ion exchange chromatography, gel filtration chromatography and immunoaffinity chromatography may be employed.

The polypeptides of the present invention have been defined by means of determined DNA and deduced amino acid sequencing. Due to the degeneracy nature of the genetic code, which results from there being more than one codon for most of the amino acid residues and stop signals, other DNA sequences which encode the same amino acid may be used for the production of the polypeptides of the present invention. In addition, it will be understood that allelic variations of these DNA and amino acid sequences naturally exist, or may be intentionally introduced using methods known in the art. These variations may be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphiphatic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine. Other contemplated variations include salts and esters of the aforementioned polypeptides, as well as precursors of the aforementioned polypeptides, for example, precursors having N-terminal substituents such as methionine, N-formylmethionine used and leader sequences. All such variations are included within the scope of the present invention.

The following examples are further illustrative of the present invention. These examples are not intended to limit the scope of the present invention, and provide further understanding of the invention.

All references cited herein are incorporated by reference in their entirety.

EXAMPLE 1

Materials and Methods

Cell Culture

COS cells were purchased from American Type Culture Collection (Rockville, Md.) and maintained in DMEM with 10% FBS, Pen+Strep, and L-Glutamine.

Construction of CD44-lg Expression Vectors

PCR was used to clone the different CD44 exons using CD44V 3-V10-lg construct (Bennett et al., (1995) *J. Cell Biol.* 128, 687–698). Oligonucleotide primers used were as follows:

CD44 V3 FP-Spe1 ACTAGTACGTCTTCAAATAC-CATCTCAG (SEQ.ID.NO.:1),

CD44 V3 RP-BamH1 GGGATCCAGGGTGCTG-GAGATAAAATCTTC (SEQ.ID.NO.:2)

CD44 E5 FP-Spe1 ACTAGTATTGTTMCCGTGATG-GCACC (SEQ.ID.NO.:3)

CD44 E5 RP-BamH1 GGGATCCGTGGTAGCAGG-GATTCTGTC (SEQ.ID.NO.:4)

CD44 V10 FP-Spe1 ACTAGTAGGAATGATGTCA-CAGGT (SEQ.ID.NO.:5)

CD44 V10 RP-BamH1 GGGATCCGTGTCTTGGTCTC-CTGATMGGAACGATTGAC (SEQ . D. NO .:6)

CD44 E15 FP-Spe1 ACTAGTGACCMGACACATTC-CAC (SEQ.ID.NO.:7)

CD44 E15 RP-BamH1 GGGATCCTCTTGACTCCCAT-GTGAGTG (SEQ.ID.NO.:8)

CD44 E16 FP-Spe1 ACTAGTCACTCACATGGGAGT-CAA (SEQ.ID.NO.:9)

CD44 E16 RP-BamH1 GGGATCCGCCMGGCCAA-GAGGGATGC (SEQ.ID.NO.:10)

CD44 V3 mutant (SGSG—AGAG) was made by changing Serine 293 and Serine 295 to Alanines using CD44

V3 mt RP-BamH1 GGGATCCAGGGTGCTG-GAGATAAAATCTTCATCATCATCAATGCCTGCTCCAGCAAAACTGAGGTG (SEQ.ID.NO.: 11).

PCR reaction conditions were as follows: 94° C. for 5 min with 35 cycles of 94° C. for 30 sec, 57° C. for 1 min, and 72° C. for 1 min 45 sec. PCR products were purified with Qiaquick spin PCR purification kit (Qiagen Corp., Chatsworth, Calif.). PCR products were digested with enzymes Spe1 and BamH1 (Boehringer Mannheim Corp.), gel purified and ligated into Spe1/BamH1 cut vector CDM8 with CD5 signal sequence 5' and human lg region Rg 3' of CD44 insert as described Peach et al., (1993) *J. Cell Biol.* 122, 257–264. All constructs were checked for the correct sequence. Primers used for the preparation of the primary strands of CD44 V3$_{E5/8aa}$ were CD44 V3-FP-Spe1 with CD44 V3a-RP AGTGCTGCTCCTTTCACTGGAGGAGC-CTGATCCAGAAAAGCTTAGGT GTCTGTC (SEQ.ID.NO.:18) and CD44 V3b-FP TCCTCCAGT-GAAAGGAGCAGCACTTCCAGCACC ATTTCAACCA-CACCACGG (SEQ.ID.NO.:19) with CD44 V4b-RP CGGATTTGMTGGCTTGG (SEQ.ID.NO.:20). These two primary reactions were then mixed and amplified by PCR using primers CD44 V3-FP-Spe1 and CD44 V3c-RP-BamH1 GGGATCCAGGGTGCTGGAAGTGCTGCTCCT (SEQ.ID.NO.:21). Primers used for primary strands of E5$_{V3/8aa}$ were CD44 E5-FP-Spe1 with CD44 E5a-RP GATAAAATCTTCATCATCATCGATGC-CGCTGCTCACGTCATCATCAGT (SEQ.ID.NO.:22) and CD44 E5b-FP ATCGATGATGAAGATTTTATCTCAG-GAGGTTACATCTTTTACACC (SEQ.ID.NO.:23) with CD44 E5-RP-BamH1. These two primary reactions were then mixed and amplified by PCR using oligonucleotide primers CD44 E5-FP-Spe1 and CD44 E5-RP-BamH1. The resulting mutant PCR products V3$_{E5/8aa}$ containing SSS-ERSST in place of IDDDEDFI and E5$_{V3/8aa}$ containing IDDDEDFI in place of SSSERSST were digested with Spe1 and BamH1 (BMC) and ligated into CDM7B vector with CD5 signal sequence and human lg constant domains as described above. Introduction of the mutations was confirmed by DNA sequencing.

Metabolic Labeling and Enzymatic Digestion

COS cell CD44-lg fusion protein was produced by using a DEAE-dextran transfection procedure with approximately $10^7$ cells as described by Aruffo et al., (1990) Cell 61,1303–1313. After DMSO shock and overnight recovery in DMEM with 10% FBS, cells were cultured in sulfate free media without FBS and labeled with 500mCi of [$^{35}$S] NaHSO$_4$(New England Nuclear, Boston, Mass.) for 36 hr. Cells were also labeled with 150 mCi/ml of 6-[$^3$H]GlcN (New England Nuclear, Boston, Mass.) for 24 hr. in DMEM media. Labeled supernatants were batch purified with Protein A sepharose (Repligen, Cambridge, Mass.), washed with PBS containing Tween-20 (0.05%) and aliquoted equally. One aliquot was left untreated, others were digested for one hour at 37° C. with 50 mU Proteus vulgaris chondroitin ABC lyase, 1 mU Flavobacterium heparinum heparitinase (ICN Immunobiologicals, Lisle, Ill.), or both. Samples were washed again in PBS containing Tween-20 (0.05%), heated for 10 min at 95° C. in 2×sample buffer with b-mercaptoethanol and analyzed on 8–16% Tris-glycine SDS-PAGE gradient gels (Novel, San Diego, Calif.). Gels were fixed and soaked in Amplify solution (Amersham Corp., Arlington Heights, Ill.). Dried gels were then analyzed by PhosphorImager (Molecular Dynamics, Sunnyvale, Calif.) for the presence or absence of modifying sulfate label on fusion proteins.

Cleavage with Cyanogen Bromide

CD44V3-Rg fusion protein was reconstituted in 100 ml of 70% formic acid, and a solution of cyanogen bromide (30 mg/100 ul) in 70% formic acid was added to provide a 1 000-fold molar excess over methionine. The reaction proceeded under a nitrogen cushion for 4 h at 30° C. and for an additional 18 h at 22° C. in the dark. The digest was vacuum-, reconstituted in 100 ul of 0.4 M Tris-HCl, pH 8.5, containing guanidine-HCl (6M) and Na$_2$EDTA (0.1%), and reduced with dithiothreitol (0.02 M) at 50° C. for 2 h. Samples were subsequently S-pyridylethylated with 4-vinylpyridine (0.10 M) for 4 h at 22° C. The reaction mixture was acidified to pH 2.0 with 20% trifluoroacetic acid (TFA) and the cyanogen bromide peptides were separated by high performance liquid chromatography (HPLC) with a Bio-Sil TSK-250 (7.5×600 mm) gel filtration column.

Cleavage with ASP-N Protease

Cleavage of the cyanogen bromide peptides of V3-wt-Rg and V3-mt-Rg fusion proteins with Pseudomonas fragi Asp-N protease was done in 40 ul of 0.1 M Tris-acetic acid buffer containing 2M urea, 4 pH 8.0, at 37° C. for 16 hr. The enzyme to substrate ratio was 1 to 25. The enzymatic digests were acidified with 10% TFA to pH 2.0 and separated by reverse-phase HPLC.

Amino Acid Sequence Analysis

Automated sequence analysis was performed in a pulsed-liquid protein sequencer (Model 476A, Applied Biosystems), using manufacturer-released cycle programs-Maresh et al., (1994) Arch. Biochem. Biophys. 311, 95–102.

Preparation of Small Oligosaccharides from V3-Rg

V3-wt-Rg was digested with heparitinase I (5U) for 24 hr. in PBS at 37° C. The digested material was separated by chromatography on a Sephadex G-50 column (1×100 cm) that was equilibrated with 10 mM phosphate buffer containing 1.0 M NaCl, pH 7.0. The column was calibrated with [$^{14}$C] glucose oligomers. Fractions corresponding to 6–10 glucose sugar residues were pooled and desalted with a Bio-Gel P-2 column (1×40 cm). [$^{3}$H]-GlcN labeled V3-Rg was used as a tracer for oligosaccharide purification.

Monosaccharides Analysis

Mild acid hydrolysis of the glycopeptides was done in 2 M TFA at 100° C. for 4 hr. Samples were analyzed by high performance anion-exchange chromatography on a BioLC System (Dionex) using a 4×250 mm CarboPac PA1 column (Dionex) using the conditions described previouslyHardy (1989). Complex Carbohydrates (Abelson, J. M. et al., eds) 77–78.

Anion-exchange Chromatography of Heparan Sulfate Disaccharides

To identify HS, fractions from a Bio-Sil TSK column were pooled and treated with heparitinase I (0.1 U/ml *Flavobacterium heparinum* EC 4.2.2.8, from ICN, Costa Mesa, Calif.) at PBS for 16 h at 37° C. Some samples were treated with heparitinase I and 2 U of heparinase I (*Flavobacterium heparinum* EC 4.2.2.7 Sigma, St. Louis, Mo.). The reaction was stopped by heating to 80° C. for 5 and then adding 1 ml 95% ethanol. After centrifugation, supernatants were collected and dried for analysis. HS disaccharides were separated on a CarbPac-PA-1 column on Dionex HPLC as described by Hascall {1 649}. The working solutions for CarboPac PA1 chromatography consisted of three solutions: solution 1 (water), solution 2 (0.2 M NaOH) and solution 3 (1.0 M TFA in 0.2 M NaOH).

The programmed gradient was (% solution 1, % solution 2, % solution 3): 0 min (50:48:2), 12 min (50:48:2), 32 min (50:37:13), 42 min (50:37:13), 62 min (50:20:30), 72 min (50:20:30), 82 min (50:0:50), 92 min (50:0:50) at 1 ml/ min. Sample was injected and isocratic elution was performed at 50:48:2 (% solution 1:2:3) for 10 min before starting gradient program. Oligosaccharide standards used were DUA-GlcN, DUA-GlcNAc, DUA-GlcNS, DUA-GlcN-6S, DUA-GlcNAc6S, DUA2S-GlcN, DUA2S-GlcNAc, DUA-GlcNS-6S, DUA2S-GlcNS, DUA-2S-GlcNAc-6S and DUA2S-GlcNS-6S (from Sigma) with retention time of 8, 9, 36, 39, 41, 45, 47, 62, 66, 72 and 87 min., respectively, by above gradient program. Control enzyme digestion was done with heparan sulfate (bovine kidney, Sigma) and heparin (porcine intestinal, Sigma, St. Louis, Mo.). In our laboratory, the Dionex HPAE-PAD system could routinely detect disaccharide standards at range from 0.05 μg to 0.5 μg at 100 nA level. PAD sensitivity decreased with an increase of sulfation of the disaccharide, and N-acetylation also decreased PAD response. Reduced disaccharides will not decrease their retention time by PA-1 column as nonreduced disaccharides except for two non-charged disaccharides. We dedicated one column for this particular application for it is difficult to regenerate the column to the optimal condition for monosaccharide analysis.

Solid Phase Binding Assay of 125-l h-FGF to V3-Rg

Human FGF basic was obtained from R & D Systems, Minneapolis, Min.(carrier free). Iodination of bFGF was performed by using IODO-BEADS (Pierce, Rockford, Ill.) as described by manufacturer's procedure. Iodinated bFGF was separated by using a short Sephadex G-25 (Pharmacia, Piscataway, N.J.) equilibrated with 1% BSA/PBS. The specificity of iodinated bFGF is 10 mCi of $^{125}$I/mg bFGF. Falcon MicroTest III 96 well assay plate (Becton Dickinson, Lincoln Park, New Jersey) were coated with CD44 fusion protein overnight at 4° C. in TBS buffer. Coated wells were blocked with 1% BSA/PBS for 1 h at room temperature and washed with the same buffer three times. [$^{125}$I]-bFGF was added to each well (0.025 mCi) and incubated at room temperature for 1 h. Wells were washed three times and each well counted with a gamma counter.

RESULTS

Figure 1:
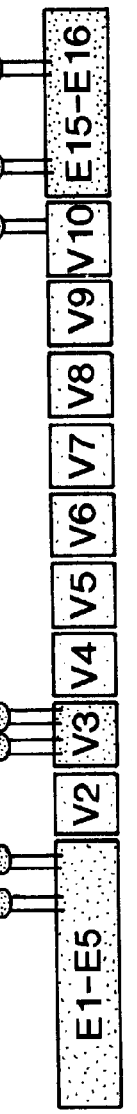
FIG. 1. CD44 and CD44 immunoglobulin fusion proteins. Line drawings representing all the CD44 extracellular domain exons and CD44-Rg constructs used in these studies. Boxes representing the variably spliced exons and standard exons are labeled V or E, respectively. The potential GAG acceptor sites are marked (∥). The boxes representing the Ig domains in the fusion proteins are labeled Ig.
Figure 1:
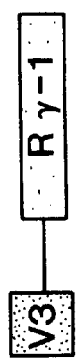
Figure 1:
Figure 1:
Figure 1:
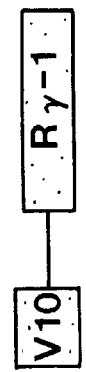
Figure 1:
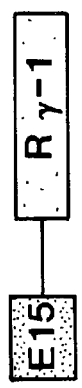
Figure 1:
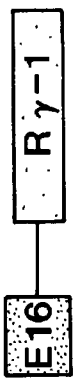
Figures 2A, 2B, 2C:
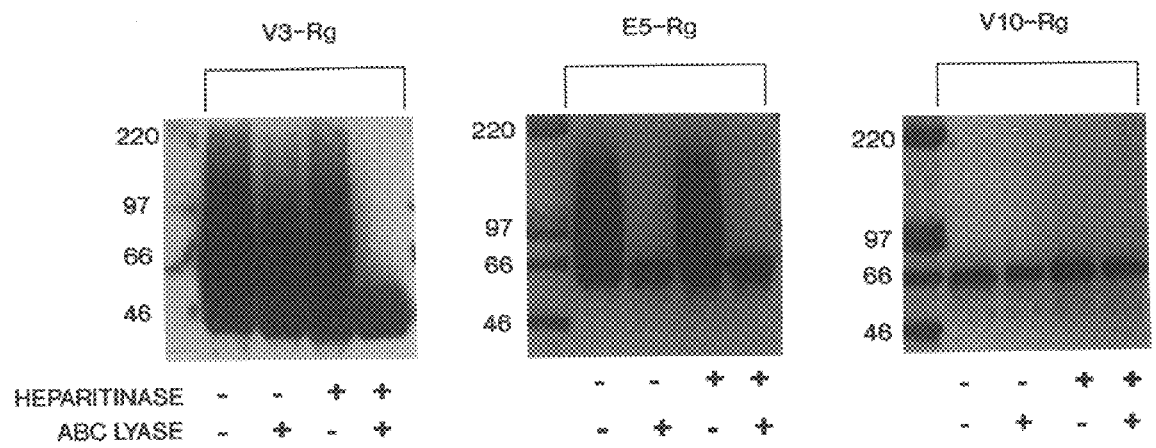
FIGS. 2A–2C. GAG modification of CD44 exons expressed as independent Rg-fusion proteins. Rg is recombinant immunoglobulin. [$^{35}$S] NaHSO$_4$ labeled (FIG. 2A) V3-Rg, (FIG. 2B) E5-Rg, (FIG. 2C) V10-Rg were recovered from the supernatant of COS cell transfectants, purified and divided equally into four aliquots. One aliquot was left untreated, the others were digested for 1 hr with Heparitinase (HEP), chondroitin ABC lyase (ABC), or with both. The proteins were then resolved by SDS-PAGE and analyzed by radiography.

HS and CS containing CD44 exons were identified by analyzing individual CD44 exons expressed separately as immunoglobulin fusion proteins (FIG. 1). The fusion proteins were analyzed for the disappearance of [$^{35}$S] NaHSO$_4$ label after enzymatic digestion and FIG. 2 demonstrates that V3-wt-Rg contains both HS and CS, and E5-Rg was modified with only CS. Unexpectedly V10-Rg was not modified with either HS or CS. The potential GAG assembly site in exon V10 is positioned at the very end of this exon. The first five amino acids of the following exon, E15 are DQDTF. Since this is a constititively expressed exon these amino acids were included in V10-Rg, thus creating a motif that is composed of acidic and hydrophobic amino acids, the hallmark for GAG synthesis. In addition, HS and CS were not detected on E15-Rg and E16-Rg proteins (data not shown). In summary, only the CD44 fusion proteins composed of exons E5 or V3 supported GAG assembly (Table 1).

HS and CS are Added to the SGSG Motif in Exon V3.

Figure 3A:
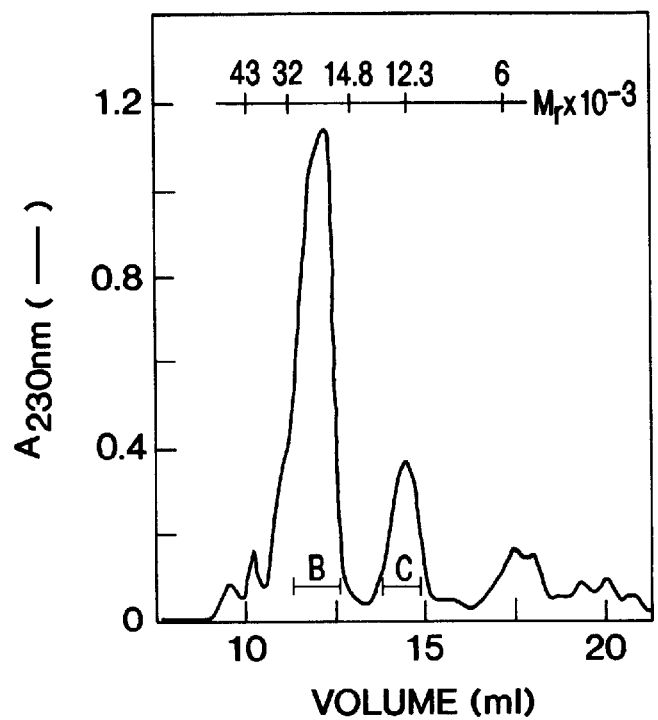
FIGS. 3A–3B. Gel permeation chromatography of V3-wt-Rg and V3-mt-Rg cyanogen bromide peptides. CNBr peptides of V3-wt-Rg and V3-mt-Rg were purified by gel permeation chromatography on a Bio-Sil TSK-250 column. Shown are the elution patterns of 1.5 nmol S-pyridylethylated peptide from V3-mt-Rg (FIG. 3A) and V3-wt-Rg (FIG. 3B). The elution volumes of ovalbumin, Mr=43,000; carbonic anhydrase, Mr=32,000; lactoalbumin, Mr=14,800; cytochrome C, Mr=12,300; and insulin, Mr=6,000, are indicated.
Figure 3B:
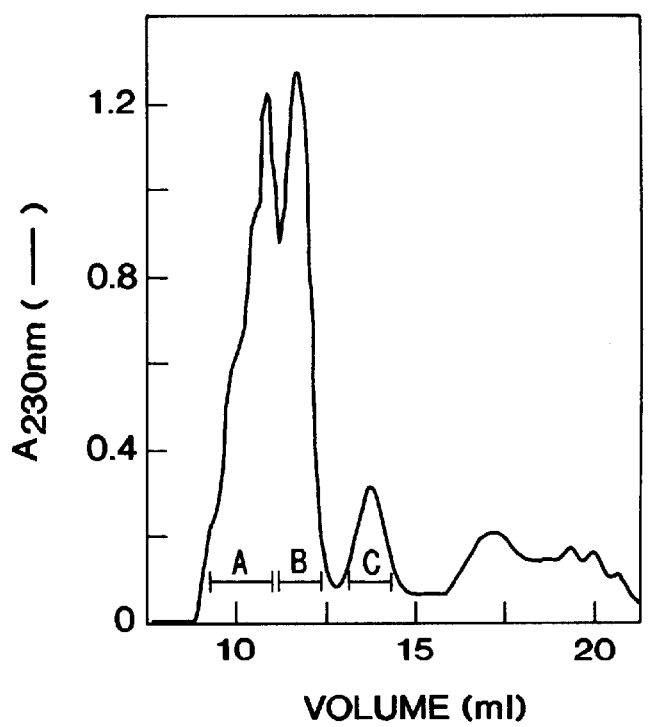

In order to establish that the SGSG motif is the site of HS and CS assembly a fusion protein, V3-mt-Rg, was made where the SGSG was mutated to AGAG (FIG. 1). This protein was analyzed for HS and CS assembly by monitoring accumulation of [$^{35}$S] NaHSO$_4$ label, followed by digestion with enzymes specific for HS and CS. These experiments demonstrated that GAG assembly did not take place on the fusion protein V3-mt-Rg. In addition, to further define the usage of the SGSG (SEQ.ID.NO.:30) site and to characterize the HS and CS assembled on exon V3 both fusion proteins, V3-mt-Rg and V3-wt-Rg, were cleaved with cyanogen bromide and the resulting peptides were purified by gel permeation chromatography and identified by aminoterminal sequence analysis (FIGS. 3A & 3B). A comparison of the profiles reveals that V3-wt-Rg contains three peptide pools (A,B,C) of distinct MW ranges, while digestion of V3-mt-Rg produced only two peptide pools (B & C). Peptide pool B generated from both fusion proteins contained the Rg domain (residues 81–256). Peptide pool C contained V3 residues 1–80. The V3-wt-Rg-cyanogen bromide pool C peptides had an apparent molecular weight of 13,500, and the apparent molecular weight of V3-mt-Rg is 11,500. Pool A peptides generated from cleavage of V3-wt-Rg also contained V3 residues 1–80. The apparent molecular weight of this pool was 37,000. In sharp contrast, cyanogen bromide digestion of V3-mt-Rg did not produce V3 containing peptides at the higher molecular weight. Enzymatic digestion was used to identify which peptide pools contained HS and CS: V3-wt-Rg pool A was the only pool that contained the two GAGs. HS and CS were released from pool A by beta elimination. The molar ratio of HS to CS was 3 to 2. These results demonstrate that both HS and CS assembly occurs at the SGSG (SEQ.ID.NO.:30) motif in CD44 exon V3.

Figure 4A:
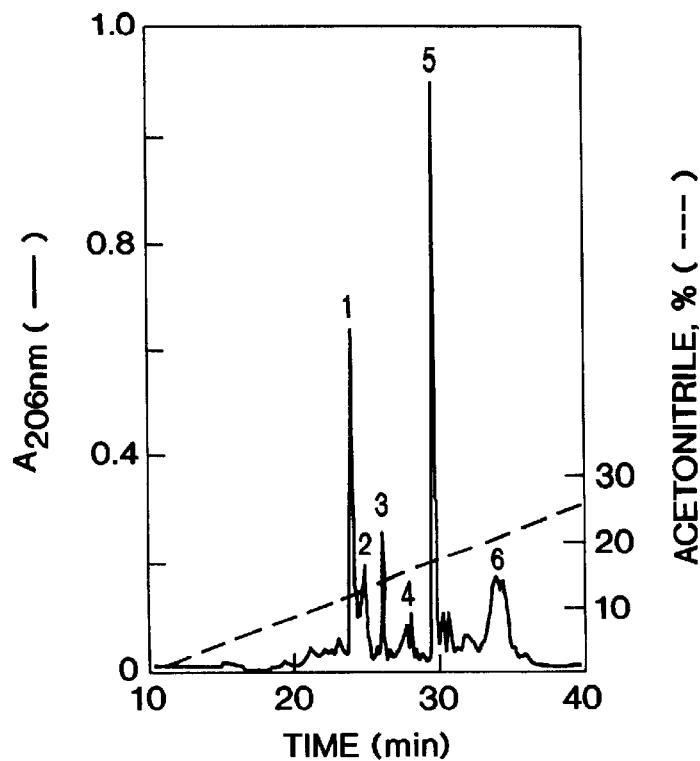
FIGS. 4A–4B. Reversed-phase high-performance liquid chromatography of V3-wt-Rg and V3-mt-Rg-peak C CNBr peptide after further digestion with Asp-N protease. The peptides were separated on a 2.1×100-mm RP-300 column. The elution pattern is shown for 150 pmol of the peptides from V3-mt-Rg (FIG. 4A) and 150 pmol of the peptides from V3-wt-Rg (FIG. 4B). Elution of the peptides was achieved with an 60-min gradient of 0.1% TFA in water to 45% acetonitrile containing 0.1% TFA at a flow rate of 100 ml/min. at 40 C.
Figure 4B:
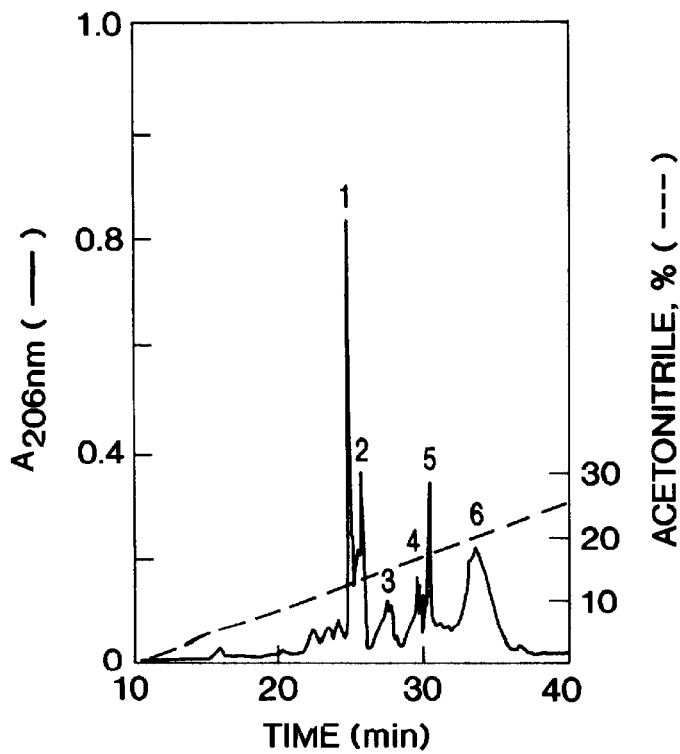

It was also desired to determine if both serines of the SGSG (SEQ.ID.NO.:30) motif in V3-wt-Rg were being utilized for GAG modification. To carry out this analysis smaller V3 peptide fragments were required. Peptide pool A was resistant to V8 and Asp-N proteases. Protease sensitive V3-wt-Rg peptide pool C was found to be modified with xylose which is the GAG precursor linkage oligosaccharide. Therefore, pool C peptides were cleaved with Asp-N protease and the resulting peptides were separated by rpHPLC and analyzed by amino acid sequencing and xylose determination (FIG. 4). Two V3-wt-Rg peptides, 3 and 4, contained the sequence SGSG and were modified with xylose. Amino acid analysis and quantitative xylose determination showed that both Ser-29 and Ser-31 are occupied on 50% of the peptides.

Identification of the Sequence Motif Responsible for HS Addition in CD44 Exon V3.

The sequence signals responsible for directing HS versus CS assembly were investigated in more detail. The first SG motif in exon E5 has a stretch of acidic amino acids preceding it. In exon V3 there are acidic residues both upstream and downstream of the SGSG (SEQ.ID.NO.:30) motif. The acidic residues located downstream of the SGSG (SEQ.ID.NO.:30) tetrapeptide are flanked by hydrophobic residues. These observations are significant since a stretch of negatively charged and hydrophobic residues located proximal to a SG site have been proposed to play a role in GAG assembly at SG sites (Zhang and Esko (1994) *J. Biol. Chem.* 269,19295–19299, Fritz et al., (1994) *J. Biol. Chem.* 269, 300–307). In addition, repetitive SG sites have been shown to enhance HS assembly (Zhang et. al., (1995) *J. Biol. Chem.* 270, 27127–27135). In conclusion, in general proteoglycans that are modified with CS and HS have a control sequence including at least three acidic amino acids and at least one hydrophobic amino acid, and the control sequence is contained within 24 amino acids surrounding the GAG assembly site (Zhang et. al., (1995) *J. Biol. Chem.* 270, 27127–27135). For proteoglycans that are modified with CS alone, in general, the control sequence is contained within 24 amino acids surrounding the glycosaminoglycan assembly site (Zhang et. al., (1995) *J. Biol. Chem.* 270, 27127–27135).

To determine if the hydrophobic and acidic residues following the SGSG (SEQ.ID.NO.:30) site in exon V3 are responsible for HS modification, the eight amino acids following the SGSG (SEQ.ID.NO.:30) motif in exon V3 were exchanged with the corresponding amino acids in exon E5 ($E5_{V3/8aa}$-Rg, FIG. 5). This exchange effectively switches the addition of HS from exon V3 to exon E5 (FIG. 6). Thus, replacing SSSERSST (SEQ.ID.NO.:32) with IDDDEDFI (SEQ.ID.NO.:29) after the first SG motif in E5 results in a protein product that is modified with HS and CS (FIG. 6). On the other hand, the V3 SGSG (SEQ.ID.NO.:30) motif followed by the sequence SSSERSST (SEQ.ID.NO.:32) rather than IDDDEDFI (SEQ.ID.NO.:29) ($V3_{E5/8aa}$-Rg) is modified with CS but not HS (FIG. 6).

The presence of CD44 Exon V3 Does Not Result in the Modification of Distal SG Sites with HS.

Four constructs were made that contained either wild type or mutant V3 in combination with other CD44 exons containing SG sites (FIG. 5). Wild type exon V3 or mutant exon V3 were included in fusion proteins containing exon E5 ($E5V3_{wt}$-Rg and $E5V3_{mt}$-Rg, respectively) or exons V4-V10 ($V3_{wt}$-V10-Rg and $V3_{mt}$-V10-Rg, respectively). These exon combinations were chosen since at least one of the SG sites in E5 is modified with CS while the single SG site in V10 is not utilized. Both fusion proteins that contained wild type exon V3, $E5V3_{wt}$-Rg and $V3_{wt}$-V10-Rg, were found to be modified with both CS and HS (FIG. 7). This contrasts with the fusion proteins containing the AGAG mutation in exon V3, $E5V3_{mt}$-Rg, which was only modified with CS. In addition, $V3_{mt}$-V10-Rg was not modified with GAGs (FIG. 7).

The HS on CD44 Exon V3 Consists of High Affinity Growth Factor Binding Oligosaccharides.

The structural features of HS oligosaccharides that b-FGF binds are known (Faham (1996) *Science* 271,1116–1120). Here it is demonstrated that these structural features are a component of the HS attached to COS cell produced V3-wt-Rg. The HS from V3-wt-Rg was prepared by digesting with heparitinase 1, or with both heparitinase I and heparinase. The resulting disaccharides were analyzed by a Dionex high performance anion exchange-pulsed amperometric detection system (HPAE-PAD). The most abundant disaccharide detected was DUA-GlcNAc followed by DUA-GlcNSO$_3$ (Table 1). Co-crystalization of b-FGF and HS showed that IdoA(2SO$_4$)-GlcNAc and IdoA(2SO$_4$)-GlcNSO$_3$ make critical contacts with the b-FGF backbone, and these oligosaccharides are also components of the V3-wt -Rg HS. Confirmation of the less abundant disaccharides was conducted by analyzing [6-$^3$H]GlcN CD44 HS. b-FGF binding oligosaccharides are a component of the HS added to CD44 exon V3.

$^{125}$I-bFGF binds V3-wt-Rg but not V3-mt-Rg

[$^{125}$I]-b-FGF can bind HS-modified exon V3-wt-Rg, demonstrating that this exon when independently expressed is fully functional. This was demonstrated by adding [$^{125}$I]-b-FGF to increasing concentrations of immobilized V3-wt-Rg and V3-mt-Rg on a microtiter plate (FIG. 7). The interaction was concentration dependent and saturable. [$^{125}$I]-b-FGF did not bind to V3-mt-Rg, confirming the requirement of HS for the interaction. In addition, the interaction between [$^{125}$I]-b-FGF and V3-wt-Rg was inhibited by 20 $\mu$g/ml heparin (porcine intestinal mucosa) and by 20 $\mu$g/ml purified V3-wt-Rg-HS oligosaccharides (6–10 mers) generated by Heparitinase I digestion .

TABLE 1

Analysis of Disaccharides of $^3$H GLIcN Labeled V3-wt-Rg

| | |
|---|---|
| ΔUA-GlcNAc | 80% |
| ΔUA-GlcNSO$_3$ | 16% |
| ΔUA(2SO$_4$)-GlcNAc | 2% |
| ΔUA(2SO$_4$)-GlcNSO$_3$ | 2% |

TABLE 2

The Surrounding Sequence of the Potential Assembly Site in the CD44 Exons

| Construct | Sequence | HS | CS |
|---|---|---|---|
| E5-Rg | ...EDIYPSNPTDDDVSSGSSSERSSTSGGY... (SEQ.ID.NO.:12) | − | + |
| E15-Rg | ...DQDTFHPSGGSHTTHGSESD... (SEQ.ID.NO.:13) | − | − |
| E16-Rg | ...EGGANTTSGPIRTPQIPE... (SEQ.ID.NO.:14) | − | − |
| V3-Rg | ...EPNEENEDERDRHLSFSGSGIDDDEDFI... (SEQ.ID.NO.:15) | + | + |
| V3-AGAG-Rg | ...EPNEENEDERDRHLSFAGAGIDDDEDFI... (SEQ.ID.NO.:16) | − | − |
| V10-Rg | ...NVNRSLSGDQDTFHP... (SEQ.ID.NO.:17) | − | − |

EXAMPLE 2

Materials and Methods

Cell Culture.

COS cells were purchased from American Type Culture Collection (Rockville, Md.) and maintained in DMEM (Gibco Life Technologies, Gaithersburg, Md.) with 10% FBS, penicillin (100 U/ml), streptomycin (100 mg/ml), and 2 mM L-glutamine.

Construction of LFA-3 and VCAM-1 Artificial Proteoglycan Expression Vectors.

The LFA-3-Rg construct was previously described (Kanner et. al., (1992) *J. Immunol.* 148, 2023–2029). Oligonucleotide primers used for inserting the CD44 V3 eight amino acid motif after the Ser-Gly present in the extracellular domain of LFA-3 were: LFA-3-FP-Hind3 AAGCTTCGACGAGCCATGGTTGCT (SEQ.ID.NO.:24) LFA-3-RP8aa-BamH1 GGGATCCCCGATAAAATCTTCATCATCATCAATACC GCTGCTTGGGATACAGGT (SEQ.ID.NO.:25). PCR product was digested with Hind3 and BamH1 (BMC), gel purified and ligated into an Ig containing mammalian expression vector as described above.

For constructing LFA-3 extracellular domain with complete CD44 V3 domains, primers used were LFA-3-FP-Hind3 and LFA-3-RP-Spe1 ACTAGTTCTGTGTCTTG AATGACCGCT (SEQ.ID.NO.:26). PCR products were digested with Hind3 and Spe1 (BMC), gel purified and ligated into Hind3 and Spe1 (BMC) cut V3$_{wt}$-Rg or V3$_{E5/8aa}$-Rg expression vectors described above.

PCR of constructs containing VCAM-1 extracellular domain using VCAM-17 lg was performed as previously described in Chan and Aruffo (1993) *J. Biol. Chem.* 268, 24655–24664. Oligonucleotide primers used were from the CMV region of the CDM8 (Seed (1987) *Nature* 329, 840–842) expression vector CMV-FP3 GTACGGGCCA-GATATACGCGTTGACATTG ATTA (SEQ.ID.NO.:27) and VCAM-1-RP3-Spe1 ACTAGTTCGGATGGTATAGGCGC-CATC (SEQ.ID.NO.:28). The PCR product was digested with Mlu1 and Spe1 (BMC), gel purified and ligated into Mlu1 and Spe1 (BMC) cut V3$_{wt}$-Rg or V3$_{E5/8aa}$-Rg expression vectors described above. All constructs were sequenced.

Metabolic labeling and Enzymatic Digestion.

The Ig fusion proteins were produced and radiolabeled with [$^{35}$S] NaHSO$_4$ (New England Nuclear, Boston, Mass.) and purified using sepharose (Repligen, Cambridge, Mass.) as previously described in Bennett et al., (1995) *J. Cell Biol.*128, 687–698.

The labeled protein was divided into four aliquots. One aliquot was left untreated, others were digested for 1 hour at 37° C. with 50mU *Proteus vulgaris* Chondroitin ABC Lyase, 2mU *Flavobacterium heparinum* Heparitinase (ICN Immunobiologicals, Costa Mesa, Calif.), or both enzymes. Samples were washed in PBS+0.05% Tween-20, heated for 10 minutes at 95° C. in 2×sample buffer containing SDS with β-mercaptoethanol and analyzed on 8–16% Tris-glycine SDS-PAGE gels (Novex, San Diego, Calif.). Gels were fixed, and soaked in Amplify solution (Amersham Corp., Arlington Heights, Ill.). Gels were dried, then analyzed using a PhosphorImager (Molecular Dynamics, Sunnyvale, Calif.).

T Cell Costimulation Assays.

U-bottom 96-well microtiter plates (Corning Corp., Corning, New York) were coated overnight with a combination of goat F(ab')$_2$ anti-human IgG (for capture of LFA-3-Rg) and goat F(ab')$_2$ anti-mouse IgG (for capture of murine anti-CD3 MAb), each at a concentration of 10 μg/ml in carbonate-bicarbonate buffer (10 mM Na$_2$CO$_3$, 40 mM NaHCO$_3$, pH 9.6). LFA-3-Rg and anti-CD3 MAb (clone 64.1, generously provided by Dr. J. Ledbetter, Bristol-Myers Squibb, Seattle, Was.) were incubated on the plates for 3 hours while T cells were isolated from normal human peripheral blood. Whole blood was passaged over Lymphocyte Separation Medium (Organon, West Chester, Pa.) and the resulting PBL (Peripheral Blood Lymphocytes) fraction was applied to a T Cell Enrichment Column (R&D Systems, Minneapolis, Minn.). Purified T cells were added to the plates at 5×10$^4$ cells/well, incubated at 37° C. with 6% CO$_2$ for 96 hours, and pulsed with 1 μCi/well $^3$H-thymidine (Amersham, Arlington Heights, Ill.) for an additional 18 hours. The plates were then harvested and counted on a beta scintillation counter. Results are expressed as the mean number of counts per minute for triplicate wells± SD.

Binding ELISAs

Immulon II 96-well microtiter plates (Dynatech Laboratories, Alexandria, Va.) were coated with LFA-3N3$_{wt}$-Rg or LFA-3-Rg at a concentration of 10 μ/ml in carbonate/bicarbonate buffer overnight at 4° C. All subsequent steps were performed at room temperature. The plates were washed 3 times and blocked with 2% BSA in PBS for 1 hour. Recombinant human b-FGF or RANTES (R&D Systems, Minneapolis, Minn.) was added to the wells and incubated for 1 hour. Goat anti-sera specific for b-FGF or RANTES (R&D Systems) at 1 μg/ml was incubated for 1 hour followed by donkey anti-goat IgG conjugated to horseradish peroxidase (Jackson ImmunoResearch, West Grove, Pa.) at 1:10,000 for 1 hour. Chromogen-Substrate solution (Genetic Systems Corp., Seattle, Wash.) was added to the wells for 15 minutes. The reaction was stopped by the addition of 1.0 N H2SO4, and the ratio of the absorbance at 450–630 nm was read. Inhibition of b-FGF or RANTES binding was tested by treating LFA-3N3$_{wt}$-Rg-coated wells with heparitinase or chondroitin ABC lyase (ICN Biochemicals) at concentrations of 0.07 unit/ml and 3.3 units/ml, respectively (in phosphate-buffered saline containing 50 mM NaOAc and 1 mM CaCl$_2$, pH 7.8), 1 hour at 43° C., before proceeding with the assay as described above. Results are expressed as the mean value of triplicate wells±standard deviation.

Results
Generation of Artificial Proteoglycans Modified with HS and CS.

In example 1 it is shown that a recombinant immuglobulin (Rg) fusion protein containing CD44 exon V3 supports CS and HS assembly, and that the proteoglycan is able to bind b-FGF. In addition, a V3 fusion protein ($V3_{E5/8aa}$-Rg that only supports CS assembly was created.

Two recombinant fusion proteins were generated. The first fusion protein generated was a GAG modified LFA-3 (CD58) immunoglobulin (Rg) fusion protein. To generate a recombinant LFA-3 proteoglycan, the Rg chimeric gene was altered to place the sequence encoding for CD44 exon V3 between the LFA-3 extracellular domain and the Rg domain, thereby creating LFA-3/$V3_{wt}$-Rg (FIG. 9). Analysis of the GAG modification on LFA-3/$V3_{wt}$-Rg showed that the proteoglycan was modified with CS and HS (FIG. 10A). A second GAG modified fusion protein was generated. In this case CD44 exon V3 was inserted into the VCAM Rg chimeric gene, creating VCAM-1/$V3_{wt}$-Rg (FIG. 9). This fusion protein also supported assembly of HS and CS (FIG. 10B).

CS-modified LFA-3 and VCAM-1Ig fusion proteins were produced. LFA-3/$V3_{E5/8aa}$-Rg and VCAM-1/$V3_{E5/8aa}$-Rg are modified exclusively with CS (FIG. 13). These findings demonstrate that inclusion of the CD44 derived $V3_{E5/8aa}$ domain results in a CS modified proteoglycan (FIG. 9B).

The Functional Domains of the Artificial Proteoglycans are Active.

Comparison of the ability of the LFA-3-Rg and LFA-3/$V3_{wt}$-Rg to drive T cell proliferation in the presence of suboptimal concentration of anti-CD3 mAb showed that inclusion of the CD44 derived sequences and GAG modification does not affect the ability of the LFA-3 moiety to bind CD2 and engage its costimulatory function (FIG. 11). The ability of LFA-3/$V3_{wt}$-Rg to costimulate T cells is dependent on LFA-3 since it could be specifically blocked with an anti-LFA-3 mAb but not a control isotype matched mAb.

Next, the growth factor and chemokine binding capability of the LFA-3/$V3_{wt}$-Rg fusion protein was tested. The ability of b-FGF to bind LFA-3-Rg and LFA-3/$V3_{wt}$-Rg was examined. As shown in FIG. 12A, b-FGF binds to LFA-3/$V3_{wt}$-Rg in a concentration dependent fashion and does not bind to LFA-3-Rg. The binding to LFA-3/$V3_{wt}$-Rg is abolished by pretreatment with heparitinase but not chondroitin ABC lyase (FIG. 12B), indicating the binding of b-FGF is mediated by HS and not CS. Heparin and heparan sulfate are also shown to compete with b-FGF for binding to LFA-3/$V3_{wt}$-Rg (FIG. 12C).

The chemokine RANTES (Regulated upon Activation, Normally T cell Expressed and Secreted) was also tested for binding to the artificial proteoglycans. Like b-FGF, RANTES shows binding to LFA-3/$V3_{wt}$-Rg and not to LFA-3-Rg (FIG. 14A). However, a pattern different from that of b-FGF is observed for the interaction of RANTES with the artificial proteoglycan modified with only HS or CS. Neither heparitinase nor chondroitin ABC lyase alone reduces RANTES binding to the GAG modified LFA-3/$V3_{wt}$-Rg; however, a combination of the two enzymes eliminates binding (FIG. 14B). Thus, while b-FGF binds only HS, RANTES is capable of binding both CS and HS. The different binding patterns of various growth factors and chemokines to CS and HS allow a means to manipulate the types and activity of GAG-binding proteins via artificial proteoglycans containing different GAGs. Artificial proteoglycans containing the CD44 exon E5 or the CD44 mutant V3 exon, $V3_{E5/8aa}$, (or any proteoglycan modified with only CS) would be expected to bind a different subset of chemokines and growth factors than the CD44 exon V3 (or any proteoglycan modified with both HS and CS).

EXAMPLE 3
Construction of LFA-3/E5wt-Rg

To construct an artificial proteoglycan expression vector that is only modified with CS the vector LFA-3/$V3_{wt}$-Rg can be digested with Spe I and BamHI to drop out the $V3_{wt}$ sequence. The sequence from exon E5, which is only modified with CS, can be recovered from vector $E5_{wt}$-Rg by similarly digesting with Spe I and BamHI. Following gel purification of the vector backbone from the $V3_{wt}$ and gel purification of exon E5 the two DNA fragments can be ligated together to make the final vector LFA-3/$E5_{wt}$-Rg.

EXAMPLE 4
Construction of an Artificial Proteoglycan Containing a Targeting Polypeptide Other that LFA-3

The above expression vectors can be used to exchange LFA-3 with any other targeting sequence. This can be done by digesting LFA-3/$V3_{wt}$-Rg with Hind III and Spe I which will create two DNA fragments: One containing the vector backbone (CDM8) plus $V3_{wt}$-Rg; the second containing the LFA-3 sequence. Gel purification can be used to purify the $V3_{wt}$-Rg containing vector and by using RT-PCR technology any targeting sequence can be amplified with Hind III and Spe I restriction sites on the ends so that it can be inserted into the vector.

EXAMPLE 5

Construction of an Artificial Proteoglycan Using Proteoglycans Other that CD44 V3 and CD44 E5.

Any proteoglycan sequence that contains a GAG assembly site and a control sequence can be inserted into LFA-3/$V3_{wt}$-Rg by first removing $V3_{wt}$. This can be done by cutting the vector with SpeI and BamHl and by using RT-PCR technology to amplify up the sequence of interest with SpeI and BamHI restriction sites and then ligating the two DNA fragments together.

What we claim is:

1. An artificial proteoglycan which is LFA-3/V3$_{wt}$-Rg.

\* \* \* \* \*